(12) United States Patent
Park et al.

(10) Patent No.: US 12,195,537 B2
(45) Date of Patent: Jan. 14, 2025

(54) ANTI-4-1BB ANTIBODY AND USE THEREOF

(71) Applicant: ABL Bio Inc., Seongnam-si (KR)

(72) Inventors: Eunyoung Park, Seongnam-si (KR);
Yangsoon Lee, Seongnam-si (KR);
Hyejin Chung, Seongnam-si (KR);
Uijung Jung, Seongnam-si (KR);
Youngdon Pak, Seongnam-si (KR);
Jun Hyun Jeong, Seongnam-si (KR);
Yeunju Kim, Seongnam-si (KR);
Seawon Ahn, Seongnam-si (KR);
Byungje Sung, Seongnam-si (KR)

(73) Assignee: ABL BIO, INC., Seongnam-si (KR)

( * ) Notice: Subject to any disclaimer, the term of this patent is extended or adjusted under 35 U.S.C. 154(b) by 791 days.

(21) Appl. No.: 17/296,752

(22) PCT Filed: Dec. 2, 2019

(86) PCT No.: PCT/KR2019/016863
§ 371 (c)(1),
(2) Date: May 25, 2021

(87) PCT Pub. No.: WO2020/111913
PCT Pub. Date: Jun. 4, 2020

(65) Prior Publication Data
US 2022/0242961 A1 Aug. 4, 2022

Related U.S. Application Data

(60) Provisional application No. 62/773,239, filed on Nov. 30, 2018.

(51) Int. Cl.
| | | |
|---|---|---|
| *G01N 31/00* | (2006.01) | |
| *A61P 35/00* | (2006.01) | |
| *C07K 16/28* | (2006.01) | |
| *C07K 16/46* | (2006.01) | |
| *G01N 33/53* | (2006.01) | |

(52) U.S. Cl.
CPC .......... *C07K 16/2827* (2013.01); *A61P 35/00* (2018.01); *C07K 16/2878* (2013.01); *C07K 16/468* (2013.01); *C07K 2317/21* (2013.01); *C07K 2317/24* (2013.01); *C07K 2317/31* (2013.01); *C07K 2317/34* (2013.01); *C07K 2317/565* (2013.01); *C07K 2317/622* (2013.01); *C07K 2317/64* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 11,891,445 B1 * | 2/2024 | Park .................. | C07K 16/2827 |
| 2014/0178368 A1 | 6/2014 | Sharp et al. | |
| 2016/0244528 A1 | 8/2016 | Gray et al. | |
| 2017/0355756 A1 * | 12/2017 | Julien ................... | C07K 16/18 |
| 2018/0258177 A1 | 9/2018 | Kwon et al. | |

FOREIGN PATENT DOCUMENTS

| | | | |
|---|---|---|---|
| JP | 2006-500921 | 1/2006 | |
| JP | 2013-544756 | 12/2013 | |
| JP | 2018-527939 | 9/2018 | |
| WO | 2005-035584 | 4/2005 | |
| WO | WO-2008068048 A2 * | 6/2008 | ............. A61P 31/10 |
| WO | 2012-032433 | 3/2012 | |
| WO | 2017-181034 | 10/2017 | |
| WO | 2017-182672 | 10/2017 | |
| WO | 2017-205745 | 11/2017 | |
| WO | 2018-045110 | 3/2018 | |

OTHER PUBLICATIONS

Mariuzza et al. (Annu. Rev.Biophys. Biophys. Chem., 16:139-159, 1987) (Year: 1987).*
Chester et al ( Blood, 131:49-57, 2018) (Year: 2018).*
KIPO, PCT Search Report & Written Opinion of PCT/KR2019/016863 dated Mar. 24, 2020.
Sambrook et al., Molecular Cloning: A Laboratory Manual, 4th ed., Cold Spring Harbor Laboratory Press, Cold Spring Harbor, N.Y. (2012).
Ausubel et al., Current Protocols in Molecular Biology, Greene Publishing Associates, Dec. 4, 2003 (ISBN: 047150338X).
Zheng-Rong Chen et al., "Therapeutic effects of antieB7-H3 antibody in an ovalbumin-induced mouse asthma model", Ann Allergy Asthma Immunol 111 (2013) 276-281.
Russell et al., "Structural Features can be Unconserved in Proteins with Similar Folds", J. Mol Biol., 244: 332-350 (1994).
John Devereux et al., "A comprehensive set of sequence analysis programs for the VAX", 1984, Nucl. Acid Res. 12:387.
M.O. Dayhoff et al., "A Model of Evolutionary Change in Proteins", 1978, Atlas of Protein Sequence and Structure 5:345-352.
Steven Henikoff et al., "Amino acid substitution matrices from protein blocks", 1992, Proc. Natl. Acad. Sci. U.S.A. 89:10915-10919.
Saul B. Needleman et al., "A General Method Applicable to the Search for Similarities in the Amino Acid Sequence of Two Proteins", 1970, J. Mol. Biol. 48:443-453.
Songsivilai and Lachmann, "Bispecific antibody: a tool for diagnosis and treatment of disease", 1990, Clin. Exp. Immunol. 79:315-321.
Sheri A. Kostelny et al., "Formation of a bispecific antibody by the use of leucine zippers.", J Immunol 1992; 148:1547-1553.

(Continued)

*Primary Examiner* — Lisa V Cook

(74) *Attorney, Agent, or Firm* — Bryan D. Zerhusen, Esq.; Nicholas R. Herrel, Esq.; CANTOR COLBURN LLP

(57) ABSTRACT

Provided is an anti-4-1BB antibody or an antigen-binding fragment thereof, and uses thereof.

4 Claims, 15 Drawing Sheets

Specification includes a Sequence Listing.

(56) References Cited

OTHER PUBLICATIONS

Chothia and Lesk, "Canonical Structures for the Hypervariable Regions of Immunoglobulins", J. Mol. Biol. 196:901-917 (1987).
Hye Young Yang et al., "Construction of a Large Synthetic Human scFv Library with Six Diversified CDRs and High Functional Diversity", Mol. Cells OT, 225-235, Feb. 28, 2009.
EPO, Extended European Search Report of the corresponding European Patent Application No. 19890588.7. dated Jul. 28, 2022.
Segal, Neil H., et al. "Results from an Integrated Safety Analysis of Urelumab, an Agonist Anti-CD137 Monoclonal Antibody." Clinical Cancer Research 23.8 (Oct. 18, 2016): 1929-1936.

* cited by examiner

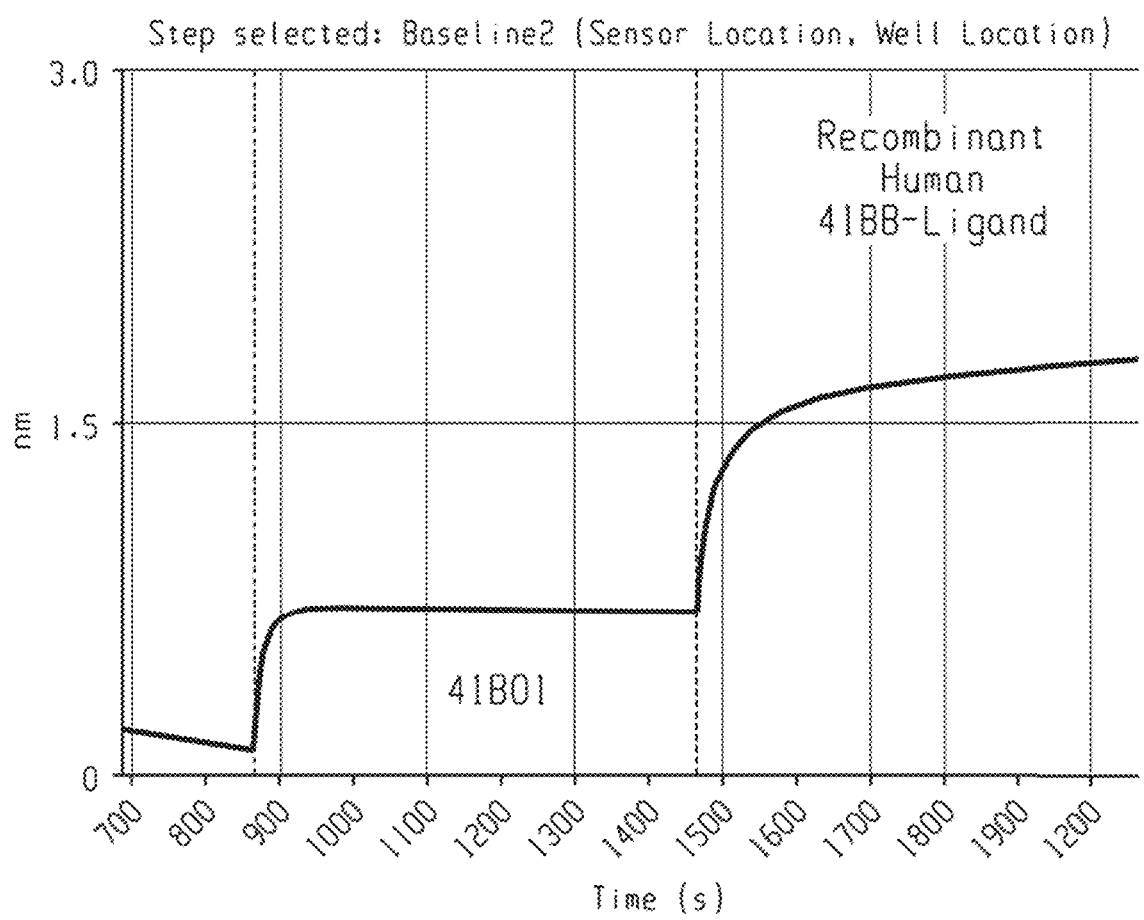

ANTI-4-1BB ANTIBODY AND USE THEREOF

CROSS-REFERENCE TO RELATED APPLICATIONS

This application claim is a National Stage entry of International Patent Application No. PCT/KR2019/016863, filed 2 Dec. 2019 and published as International Patent Application Publication No. WO 2020/111913 A1, which claims priority to and the benefit of U.S. Provisional Patent Application No. 62/773,239, filed 30 Nov. 2018, each of which is incorporated by reference herein in their entireties.

INCORPORATION BY REFERENCE

In compliance with 37 C.F.R. 1.52 (e), the sequence information contained in electronic file name: ABZ0006US2 Sequence Listing ST25 08MAY2024.txt; size TBD KB; created on: 8 May 2024, is incorporated herein by reference in its entirety.

BACKGROUND OF THE INVENTION

1. Field

Provided is an anti-4-1BB antibody or an antigen-binding fragment thereof, and uses thereof.

2. Description of the Related Art 4-1BB is a member of TNF-receptor superfamily (TNFRSF) and is a co-stimulatory molecule which is expressed following the activation of immune cells, both innate and adaptive immune cells. 4-1BB plays important role in modulate the activity of various immune cells. 4-1BB agonists enhance immune cell proliferation, survival, secretion of cytokines and cytolytic activity CD8 T cells. Many other studies showed that activation of 4-1BB enhances immune response to eliminate tumors in mice. Therefore, it suggests that 4-1BB is a promising target molecule in cancer immunology. Despite of their anti-tumor efficacy, anti-4-1BB antibody induced severe liver toxicity in clinical application.

SUMMARY

An embodiment provides an anti-4-1BB antibody or an antigen-binding fragment thereof capable of enhancing immune response and/or treating tumor (cancer) in a mammal. The anti-4-1BB antibody or an antigen-binding fragment thereof is characterized by localizing and/or activating only in tumor microenvironment (TME) and/or considerably reducing liver toxicities compared to pre-existing anti-4-1BB antibodies, with maintaining the efficacies of enhancing immune response enhancement and/or tumor treatment.

Another embodiment provides an anti-4-1BB antibody or an antigen-binding fragment thereof comprising:
- a CDR (complementarity determining region)-H1 comprising an amino acid sequence of SEQ ID NO: 1, 2, or 3;
- a CDR-H2 comprising an amino acid sequence of SEQ ID NO: 4, 5, or 6;
- a CDR-H3 comprising an amino acid sequence of SEQ ID NO: 7, 8, 9, 10, or 11;
- a CDR-L1 comprising an amino acid sequence of SEQ ID NO: 12 or 13;
- a CDR-L2 comprising an amino acid sequence of SEQ ID NO: 14 or 15; and
- a CDR-L3 comprising an amino acid sequence of SEQ ID NO: 16 or 17.

TABLE 1

CDRs of anti-4-1BB antibodies:

Heavy Chain CDRs

| CDR-H1 | CDR-H2 | CDR-H3 |
|---|---|---|
| SYDMS (SEQ ID NO: 1) | WISYSGGSIYYADS VKG (SEQ ID NO: 4) | DGQRNSMREFDY (SEQ ID NO: 7) |
| GYDMS (SEQ ID NO: 2) | VIYPDDGNTYYADS VKG (SEQ ID NO: 5) | DAQRNSMREFDY (SEQ ID NO: 8) |
| SNVMN (SEQ ID NO: 3) | EISHSGSTNYNPSL KS (SEQ ID NO: 6) | DAQRQSMREFDY (SEQ ID NO: 9) |
|  |  | HGGQKPTTKSSSAY GMDG (SEQ ID NO: 10) |
|  |  | GAGNLGY (SEQ ID NO: 11) |

Light Chain CDRs

| CDR-L1 | CDR-L2 | CDR-L3 |
|---|---|---|
| SGSSSNIGNNYVT (SEQ ID NO: 12) | ADSHRPS (SEQ ID NO: 14) | ATWDYSLSGYV (SEQ ID NO: 16) |
| QASQDISNYLN (SEQ ID NO: 13) | GASSRAT (SEQ ID NO: 15) | QQYNSYPIT (SEQ ID NO: 17) |

In an specific embodiment, the anti-4-1BB antibody or an antigen-binding fragment thereof may comprise;
- a polypeptide comprising an amino acid sequence of SEQ ID NO: 40 as a H-FR1;
- a polypeptide comprising an amino acid sequence of SEQ ID NO: 41 as a H-FR2;
- a polypeptide comprising an amino acid sequence of SEQ ID NO: 42, 43, 44, or 45 as a H-FR3;
- a polypeptide comprising an amino acid sequence of SEQ ID NO: 46 as a H-FR4;
- a polypeptide comprising an amino acid sequence of SEQ ID NO: 47, 48, or 49 as a L-FR1;
- a polypeptide comprising an amino acid sequence of SEQ ID NO: 50 or 51 as a L-FR2;
- a polypeptide comprising an amino acid sequence of SEQ ID NO: 52 or 53 as a L-FR3; and/or a polypeptide comprising an amino acid sequence of SEQ ID NO: 54 or 55 as a L-FR4.

Another embodiment provides an anti-4-1BB antibody or an antigen-binding fragment thereof comprising a heavy chain variable region comprising a CDR-H1 comprising an amino acid sequence of SEQ ID NO: 1, 2, or 3, a CDR-H2 comprising an amino acid sequence of SEQ ID NO: 4, 5, or 6, and a CDR-H3 comprising an amino acid sequence of SEQ ID NO: 7, 8, 9, 10, or 11; and a light chain variable region comprising a CDR-L1 comprising an amino acid sequence of SEQ ID NO: 12 or 13, a CDR-L2 comprising an amino acid sequence of SEQ ID NO: 14 or 15, and a CDR-L3 comprising an amino acid sequence of SEQ ID NO: 16 or 17.

Another embodiment provides an anti-4-1BB antibody or an antigen-binding fragment thereof comprising a heavy chain variable region comprising or consisting essentially of SEQ ID NO: 18, 19, 20, 21, 22, 23, 39, 57, 58, 59, or 60; and a light chain variable region comprising or consisting essentially of an amino acid sequence of SEQ ID NO: 24, 25, 26, 61, or 62.

Another embodiment provides an anti-4-1BB antibody or an antigen-binding fragment thereof comprising a heavy chain comprising or consisting essentially of an amino acid sequence of SEQ ID NO: 27, 28, 29, 30, 31, or 32; and a light chain comprising or consisting essentially of an amino acid sequence of SEQ ID NO: 33, 34, or 35.

In an embodiment, the anti-4-1BB antibody or antigen-binding fragment described herein may further comprise at least one polypeptide targeting a bioactive material other than 4-1BB.

Another embodiment provides a pharmaceutical composition comprising the anti-4-1BB antibody or an antigen-binding fragment thereof. The pharmaceutical composition may further comprise a pharmaceutically acceptable carrier. The pharmaceutical composition may be used for enhancing immune response, and/or for treating and/or preventing a cancer. The enhancing immune response may be 4-1BB signal activation, T-cell activation, or both of them.

Another embodiment provides a method of treating and/or preventing a cancer in a subject in need thereof, comprising administering to the subject a pharmaceutically effective amount of the anti-4-1BB antibody or an antigen-binding fragment thereof or the pharmaceutical composition. The method may further step of identifying the subject in need of treating and/or preventing a cancer, prior to the administering step.

Another embodiment provides a method of enhancing immune response in a subject in need thereof, comprising administering to the subject a pharmaceutically effective amount of the anti-4-1BB antibody or an antigen-binding fragment thereof or the pharmaceutical composition. The method may further step of identifying the subject in need of enhancing immune response, prior to the administering step. The enhancing immune response may be 4-1BB signal activation, T-cell activation, or both of them.

Another embodiment provides a use of the anti-4-1BB antibody or an antigen-binding fragment thereof or the pharmaceutical composition in treating and/or preventing a cancer. Another embodiment provides a use of the anti-4-1BB antibody or an antigen-binding fragment thereof in preparing a pharmaceutical composition for treating and/or preventing a cancer.

Another embodiment provides a use of the anti-4-1BB antibody or an antigen-binding fragment thereof or the pharmaceutical composition enhancing immune response. Another embodiment provides a use of the anti-4-1BB antibody or an antigen-binding fragment thereof in preparing a pharmaceutical composition for enhancing immune response. The enhancing immune response may be 4-1BB signal activation, T-cell activation, or both of them.

An embodiment provides a polynucleotide encoding the anti-4-1BB antibody or an antigen-binding fragment thereof. In particular, an embodiment provides a first polynucleotide encoding at least one of CDR-H1, CDR-H2, and CDR-H3, a heavy chain variable region, or a heavy chain of the anti-4-1BB antibody or an antigen-binding fragment thereof, as described above. Another embodiment provides a second polynucleotide encoding at least one of CDR-L1, CDR-L2, and CDR-L3, a light chain variable region, or a light chain of the anti-4-1BB antibody or an antigen-binding fragment thereof, as described above.

An embodiment provides a recombinant vector comprising the first polynucleotide, the second polynucleotide, or a combination thereof. Another embodiment provides a recombinant cell transfected with the recombinant vector.

Another embodiment provides a method of preparing the anti-4-1BB antibody or an antigen-binding fragment thereof, comprising expressing the first polynucleotide and the second polynucleotide in a cell. The step of expressing the polynucleotide may be conducted by culturing the cell comprising the polynucleotide (for example, in a recombinant vector) under a condition allowing the expression of the polynucleotide. The method may further comprise isolating and/or purifying the anti-4-1BB antibody or an antigen-binding fragment thereof from the cell culture, after the step of expressing or culturing.

The terms "antigen-binding fragment", as used herein, is a portion of an antibody with a capability of recognizing and/or binding to an antigen, which is selected from the group consisting of F(ab')2, F(ab)$_2$, Fab', Fab, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein). Immunoglobulin (e.g., a human immunoglobulin) or antibody molecules of the disclosure can be of any type (e.g., IgG, IgE, IgM, IgD, IgA, IgY, and the like), class (e.g., IgG1, IgG2, IgG3, IgG4, IgG5, IgA1, IgA2, and the like), or subclass of immunoglobulin molecule.

The term "antibody" may encompass various broad classes of polypeptides that can be distinguished biochemically. Those skilled in the art will appreciate that heavy chains are classified as gamma, mu, alpha, delta, or epsilon ($\gamma$, $\mu$, $\alpha$, $\delta$, $\epsilon$) with some subclasses among them (e.g., $\gamma1$-$\gamma4$), and light chains are classified as either kappa or lambda (K, $\lambda$). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgG5, etc. are well characterized and are known to confer functional specialization.

Antibodies and antigen-binding fragments of the disclosure may include, but not be limited to, polyclonal or monoclonal; monospecific or multispecific; and/or human, humanized, animal (e.g., mouse, rabbit, etc.), or chimeric antibodies.

The term "subject" may refer to any subject, particularly a mammalian subject, for whom diagnosis, prognosis, or therapy is desired. Mammalian subjects may include humans, domestic animals, farm animals, and zoo, sport, or pet animals such as dogs, cats, guinea pigs, rabbits, rats, mice, horses, cattle, cows, and so on.

In one aspect, antibody or fragment thereof is chemically or recombinantly synthesized (not naturally occurring).

Given that each of antibodies can bind to 4-1BB such as human 4-1BB, the CDR sequences, or $V_L$ (heavy chain variable region) and $V_L$ (light chain variable region) sequences as disclosed herein can be "mixed and matched" to create other anti-4-1BB binding molecules.

BRIEF DESCRIPTION OF THE SEVERAL VIEWS OF THE DRAWINGS

FIGS. 12A-12C show cross-competition between recombinant human 41BB-ligand and 41B01.

DETAILED DESCRIPTION

Definitions

Figure 1A:
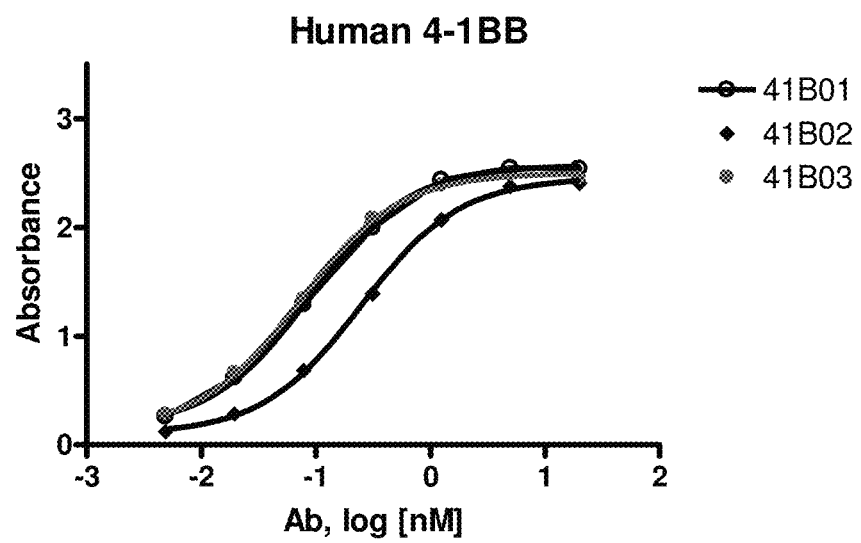
FIGS. 1A-1C show the results of analysis (ELISA) of the binding capacity to the 4-1BB antigen of the anti-4-1BB antibody prepared according to one embodiment of the present invention. It shows that each anti-4-1BB monoclonal antibody specifically binds to the extracellular domain 4-1BB antigen.

Herein, "polynucleotide" or "nucleic acid" includes a single or double strand nucleotide polymer. The nucleotide comprising such a polynucleotide may be a ribonucleotide or deoxyribonucleotide or their modified forms.

Unless otherwise stated herein, the left end of the polynucleotide stated herein is 5' end and its right end represents 3' end.

Herein, "isolated nucleic acid molecule" means DNA or RNA of genomic origin or mRNA, cDNA of synthetic origin or their combinations, which is linked to the polynucleotide that all or a portion of it is not associated with a polynucleotide present in nature, or it is not observed in nature. On the purpose of the present invention, the nucleic acid molecule comprising a specific nucleic acid sequence does not comprise an intact chromosome. Instead, the isolated nucleic acid molecule comprising a specific nucleic acid sequence may comprise at least several additional protein coding sequences, in addition to its specific sequence, or may further comprise a regulatory sequence and/or vector for expression of the specific nucleic acid sequence.

Herein, the term "regulatory sequence" means a polynucleotide sequence which can affect the expression and processing of a coding sequence by being operably connected thereto. This property of the regulatory sequence may be influenced by kinds of hosts. For example, the regulatory sequence applicable in a prokaryotic cell may include a promoter, occasionally an operator, a ribosome-binding site and a transcription termination sequence. In a eukaryotic cell, the regulatory sequence may comprise a promote comprising multiple recognition sites, a transcription enhancer, a polyadenylation sequence and a transcription termination sequence. The regulatory sequence may further comprise a reader sequence and/or a fusion partner sequence.

Herein, "vector" means any molecule used for delivering a nucleic acid molecule encoding a protein to a host cell, comprising for example, a nucleic acid, a plasmid, a bacteriophage or a virus.

Herein, "expression vector or recombinant vector" means a vector which is suitable for transformation of a host cell and comprises a nucleic acid sequence that is operably connected to an expression vector and regulates the expression of heterologous sequences encoding a targeting protein. This expression vector may be also operably connected to the coding sequence, and in case of transcription, translation and that an intron is present, it may comprise a sequence regulating RNA splicing or affecting it.

Herein, "operably (or operatively) connected (or linked)" means that nucleic acid sequences to be connected are positioned so as to perform a targeting function under an appropriate condition. For example, if the transcription of the coding sequence is affected by the regulatory sequence under an appropriate condition in a vector comprising a coding sequence and a regulatory sequence, it is operably connected.

Herein, "host cell" means a cell which can express a target gene that is transformed or to be transformed by a targeting nucleic acid sequence. The term includes progeny of the host cell, as long as expressing the targeting gene, regardless of identity of host cell and form and genetic makeup.

Herein, "transduction" commonly means movement of a nucleic acid from one bacterium to another bacterium by a bacteriophage. For example, it includes movement of a nucleic acid to a eukaryotic cell using a retrovirus which cannot replicate.

Herein, "transfection" means that a cell takes a foreign or exogenous DNA, and in this case, DNA is introduced in a cell through a cell membrane. This may refer methods known in the art, for example, Sambrook et al., Molecular Cloning: A Laboratory Manual, 4th ed., Cold Spring Harbor Laboratory Press, Cold Spring Harbor, N.Y. (2012), Ausubel et al., Current Protocols in Molecular Biology, Greene Publishing Associates.

Herein, "transformation" means a change of genetic properties of a cell, which are modified so that a cell comprises a new DNA or RNA. For example, a cell may be transformed as its genetic properties are changed, by introducing a new genetic material through transduction, transfection, or other techniques. The DNA transformed by methods including transduction or transfection, etc. may be present by being physically integrated in a chromosome of a cell, or may be temporarily present as an episome form without replication or a replicable plasmid. When the transformed DNA is replicated with division of a host cell, it is considered as stably transformed.

Herein, "amino acid" includes the common meaning understood in the art. Twenty natural-occurring amino acids and their abbreviations are as those commonly used in the art (Immunology-A Synthesis, 2nd Edition, E. S. Golub and D. R. Green, eds., Sinauer Associates: Sunderland, Mass. 1991). The amino acid includes typical amino acids, stereoisomers of typical 20 amino acids (D-amino acids), non-natural amino acids, for example, α-,α-disubstituted amino acids, N-alkyl amino acids, and other non-typical amino acids. As examples of non-typical amino acids, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine and other similar amino acids and imino acids (for example, 4-hydroxyproline). In the mark of polypeptide used herein, as commonly used in the art, the left of a sequence is an amino terminal and the right represents a carboxy terminal.

Herein, "polypeptide" or "protein" means a polymer of an amino acid residue, and it is used interchangeably herein. This also includes not only polymers of naturally occurring amino acid residues but also polymers of their analogues or mimetics. In addition, the polypeptide or protein may comprise modification such as addition of carbohydrates for phosphorylation or glycosylation, etc. Moreover, the polypeptide or protein may be produced in a recombinant or naturally found cell. Furthermore, the polypeptide or protein may include those in which a portion of a wild type sequence or the amino acid sequence is deleted, added and/or substituted. In addition, the polypeptide or protein includes an antibody, for example, an anti-4-1BB antibody (or named as 4-1BB antibody), 4-1BB binding protein, or an antigen-binding fragment, or a sequence in which one or more amino acids in the sequence are deleted, added and/or substituted. Moreover, "polypeptide fragment" means a polypeptide having an amino terminal deletion, a carboxyl terminal deletion and/or an internal deletion, compared to a full-length protein. This fragment may also include modified amino acids compared to a full-length protein. In one embodiment, the fragment may be about 5 to 500 amino acids in length, for example, at least 5, 6, 8, 10, 14, 20, 50, 70, 100, 110, 150, 200, 250, 300, 350, 400, 450, 500, 550, 600, 650, 700, 750, 800, 850 or more amino acids in length. Considering the purpose of the present invention, the useful polypeptide fragment includes an immunological functional fragment of an antibody comprising an antigen-binding domain. In case of 4-1BB binding antibody, such a useful fragment includes a CDR sequence comprising 1, 2, or 3 of heavy chains or light chains, or all or a portion of antibody chain comprising a variable region or constant region of a heavy chain or light chain, but not limited thereto.

Herein, "isolated polypeptide, antibody or protein" is that there is not any other protein to be found together with them commonly and at least about 50% or more of lipids, carbohydrates and polynucleotides naturally connected to them are removed. Typically, the isolated protein, polypeptide or antibody comprises at least about 5%, at least about 10%, at least about 25% or at least about 50%, in a certain composition. This polypeptide may be encoded by genome DNA, cDNA, mRNA or other RNA of synthetic origins or any combinations thereof. In particular, the isolated protein, polypeptide or antibody is substantially free of contaminants of other proteins or other polypeptides, which interfere with its therapeutic, diagnostic and prophylactic researches or application for other uses.

The antibody and/or its antigen-binding fragment described herein may include "variants" thereof, wherein the variant may refer a polypeptide in which one or more amino acid residues are inserted, deleted, added and/or substituted from the polypeptide sequence, so long as maintain the desired biological activity and/or structure of the antibody and/or its antigen-binding fragment, and may include a fusion polypeptide by linking to other polypeptide. In addition, the variant may include one modified by protein enzyme cutting, phosphorylation, and/or other posttranslational modification, but maintaining biological activity of the antibody and/or its antigen-binding fragment disclosed herein, for example, binding to 4-1BB and specificity. The variant may be have a sequence identity of at least 80%, at least 85%, at least 90%, at least 95%, at least 96%, at least 97%, at least 98%, or at least 99%, for example, a sequence identity of about 99%, 98%, 97%, 96%, 95%, 94%, 93%, 92%, 91%, 90%, 89%, 88%, 87%, 86%, 85%, 84%, 83%, 82%, 81%, or 80%, to the sequence of the antibody or its antigen-binding fragment disclosed herein. The percent identity (%) or homology may be calculated with reference to the following description.

In one embodiment, the percent homology or identity may be calculated as 100×[(identical position)/min(TGA, TGB)], and in the formula, TGA, TGB are the sum of the number of residues of sequences A and B compared and the internal gap position (Russell et al., J. Mol Biol., 244: 332-350 (1994).

Herein, the conservative amino acid substitution means the substitution which does not substantially affect the activity or antigenicity of a polypeptide. The polypeptide may comprise one or more conservative substitutions. Non-limiting examples are disclosed in the following Table 3.

The "derivative" of the polypeptide herein means a polypeptide chemically modified in one or more residues through conjugation with other chemical moiety, which is different from an insertion, deletion, addition or substitution variant.

The 4-1BB (Receptor Tyrosine Kinase-Like Orphan Receptor), that is recognized by the antibody or antigen-binding fragment thereof described herein, may refer to a transmembrane protein of an RTK (Receptor Tyrosine Kinase) family. In one embodiment, it particularly recognizes an extracellular domain. The 4-1BB which the antibody recognizes may be an extracellular domain which is present in a cell membrane or is not present in a cell membrane. The human protein of 4-1BB consists of 937 amino acids, and the amino acid sequence is NCBI Reference Sequence ID: NP_005003.2, and the nucleic acid sequence is NM_005012.3. Unless apparent from the context used herein, the 4-1BB refers to a human h4-1BB, but the antibody has the binding capacity to mouse 4-1BB specifically. The mouse 4-1BB amino acid sequence is represented by Gen Bank: BAA75480.1.

Herein "identity" means the sequence similarity of two or more polypeptides or two or more polynucleotides, which are determined by arranging and comparing two or more polypeptides or two or more polynucleotides. This identity between sequences is commonly represented by "identity percent", and this means the ratio of identical amino acids or nucleotides between molecules to be compared, and it is calculated on the basis of the smallest size of molecule, among molecules to be compared.

When the identity percent is calculated, sequences to be compared are arranged in the way of providing the maximum matching between sequences, and in the arranged sequences, gap, matching and mis-match may be present, and this is treated by a specific mathematical model or a computer algorithm. In one embodiment, this identity percent may be determined using a GCG program package including a GAP program which arranges two sequences in the way of maximizing the match between sequences to be compared and minimizing the number of gaps, using Needleman and Wunsch algorithm (Devereux et al., 1984, Nucl. Acid Res. 12:387; Genetics Computer Group, University of Wisconsin, Madison, WI, USA). The computer algorithm GAP determines "matching span" by arranging two sequences in the way of maximizing the match between them and minimizing the number of gaps in two polypeptide or polynucleotide sequences to be compared. The algorithm also uses a gap opening penalty [this is calculated as 3×average diagonal, wherein "average diagonal" is the average of diagonals of comparison matrix to be used; and "diagonal" is a score or number assigned for each complete amino acid match by a specific comparison matrix] and a gap extension penalty (this is commonly ⅒ fold of the gap opening penalty), and a comparison matrix, for example, PAM 250 or BLOSUM 62 together. In a specific embodiment, a standard comparison matrix (refer to Dayhoff et al., 1978, Atlas of Protein Sequence and Structure 5:345-352 for PAM 250 comparison matrix; refer to Henikoff et al., 1992, Proc. Natl. Acad. Sci. U.S.A. 89:10915-10919 for BLOSUM 62 comparison matrix) is used. In one embodiment, parameters recommended for determining the identity percent of polypeptides or polynucleotides in which the GAP program is used are as follows: algorithm: Needleman et al., 1970, J. Mol. Biol. 48:443-453; comparison matrix: BLOSUM 62 (Henikoff et al., 1992, supra); gap penalty: 12 (no penalty fora terminal gap); gap length penalty: 4; similarity threshold: 0.

When two sequences are arranged using specific parameters, although there is no significant relation between two sequences, the result that they are matched with high identity in a short sequence region may be derived. In this case, in order that two sequences are arranged through at least 50 sequential amino acids, parameters of the algorithm used as the GAP program can be corrected.

"Substantially pure" used herein is that a targeting molecule is present as a predominant species. In other words, it means that on the basis of mole, the concentration is higher than any other individual species in the same mixture. In one embodiment, a substantially pure molecule is comprised as at least about 50% (based on mole), at least about 80%, about 85%, at least about 90%, or at least about 99%, among all polymers comprised in a composition. In other embodiment, the targeting molecule is substantially homogeneously purified until any more contaminants are not detected by using a conventional method, and therefore the composition comprises one kind of homogeneous polymer material.

In one aspect, the present invention relates to a recombinant antibody specifically binding to 4-1BB protein or its antigen-binding fragment. In this aspect, "recombinant protein" is a protein prepared using a recombination technique, namely, through the expression of the recombinant nucleic acid described in the present invention. The methods and techniques for production of a recombinant protein are widely known in the art.

Herein, "affinity" is the strength of interaction between an antibody or its antigen-binding fragment and an antigen, and it is determined by properties of the antigen such as size, shape and/or charge of antigen, and CDR sequences of the antibody or antigen-binding fragment. The methods for determining the affinity are known in the art, and the followings can be referred.

The antibody or its antigen-binding fragment is called "specifically binding" to its target such as an antigen, when a dissociation constant (KD) is $10^{-6}$ M or less. The antibody specifically binds to a target with "high affinity", when KD is $1 \times 10^{-8}$ M or less.

Herein, "antigen-binding region or site" means a protein or a part of protein specifically binding to a specific antigen. For example, a part of an antibody comprising an amino acid residue providing the antibody with specificity and affinity to an antigen, by interacting with the antigen. This antigen-binding region typically comprises one or more "complementary determining regions (CDR)". A specific antigen-binding region also comprises one or more "framework (FR)" regions. The framework region helps to maintain an appropriate conformation of these CDRs, thereby facilitating binding between the antigen-binding region and an antigen.

Herein, "antibody" means an antigen-binding fragment which can compete to an intact antibody for binding to any isotype of intact immunoglobulin, or a target antigen. For example, it comprises chimeric, humanized, complete human and dual-specific antibodies or their antigen-binding fragments. The antibody is one kind of antigen binding proteins by itself. The intact antibody commonly comprises at least 2 full-length heavy chains and 2 full-length light chains, but in some cases as naturally found in Camelid animals, the antibody may comprise only heavy chains. The antibody or its antigen-binding fragment may be derived from only one source or chimeric. The chimeric antibody comprises a part derived from two kinds of different antibodies, and is described in more detail below. The antibody or its antigen-binding fragment can be produced by hybridoma, recombinant DNA technique or enzymatic or chemical cutting of an intact antibody. Unless otherwise stated, herein, the term, antibody includes an antibody comprising 2 full-length heavy chains and 2 full-length light chains, and its derivatives, variants, fragments, and mutants, and their examples are as described below.

Herein, "light chain" includes a full-length light chain having a variable region sequence enough to provide binding specificity to an antigen or epitope and its fragment. The full-length light chain comprises a variable region domain VL and a constant region domain CL. The variable region domain of light chain is present in an amino terminal of a light chain polypeptide. The kinds of light chains include kappa and lambda chains.

Herein, "heavy chain" includes a full-length heavy chain having a variable region sequence enough to provide binding specificity to an antigen or epitope and its fragment. The full-length heavy chain comprises a variable region domain VH and 3 constant region domains CH1, CH2 and CH3. The VH domain is present in an amino terminal of a heavy chain polypeptide and the CH domain is present in a carboxy terminal, and the CH3 is positioned closest to a carboxy terminal. The heavy chain comprises IgG (comprising IgG1, IgG2, IgG3 and IgG4 subtypes), IgA (comprising IgA1 and IgA2 subtypes), and isotypes of IgM and IgE.

Used herein, "antigen-binding fragment" of a chain (heavy chain or light chain) of an antibody or immunoglobulin includes a part of an antibody which lacks some amino acids compared to a full-length chain, but can specifically bind to an antigen. This fragment can be considered as having biological activity, in an aspect that it can specifically bind to a target antigen, or can compete to other antibodies or an antigen-binding fragment to bind a specific epitope. In one aspect, this fragment comprises at least one CDR present in a full-length light chain or heavy chain, and in some embodiments, it comprises a short-chain heavy chain and/or light chain, or its part. This biological active fragment may be produced by a recombinant DNA technique or may be produced for example, by cutting an intact antibody enzymatically or chemically. An immunologically functional immunoglobulin fragment includes Fab, Fab', F(ab')2, scFab, dsFv, Fv, scFV, scFV-Fc, diabody, minibody, scAb, and dAb, but not limited thereto, and may be derived from any mammal including human, mouse, rat, camelid or rabbit, but not limited thereto. The functional part of the antibody such as one or more CDRs described herein may be linked with a secondary protein or small molecular compound by a covalent bond, thereby being used as a target therapeutic agent to a specific target.

Herein, "Fc" region comprises two heavy chain fragments comprising CH2 and CH3 domains of an antibody. These 2 heavy chain fragments are combined each other by hydrophobic interaction of two or more of disulfide bonds and CH3 domain.

Herein, "Fab fragment" consists of 1 light chain and 1 heavy chain comprising a variable region and CH1 only. The heavy chain of Fab molecule cannot form a disulfide bond with other heavy chain molecule. scFab is one that two molecules of Fab is linked by a flexible linker.

Herein, "Fab' fragment" comprises a region between CH1 and CH2 domains of a heavy chain, in addition to Fab fragment, and it can form a disulfide bond between two heavy chains of two molecules of Fab' fragment, to form a F(ab')2 molecule.

Herein, "F(ab')2 fragment" comprises two light chains, and two heavy chains comprising a variable region, CH1 and a part of a constant region between CH1 and CH2 domains, as aforementioned, and thereby an intrachain disulfide bond between 2 heavy chains is formed. Thus, the F(ab')2 fragment consists of two Fab' fragments, and the two Fab' fragments are meeting each other by the disulfide bond between them.

Herein, "Fv region" is a fragment of an antibody which comprises each variable region of a heavy chain and a light chain, but does not comprise a constant region. sdFV is one that a heavy chain and a light chain are linked by a disulfide bond. scFc is one that single stranded variable regions (Fv) of heavy chain and light chain are linked via a flexible linker. scFv-Fc is one that Fc is linked to scFV. The minibody is one that CH3 is linked to scFV. The diabody comprises two molecules of scFV.

Herein, "short-chain antibody (scAb)" is a single polypeptide chain comprising one variable region of a heavy chain or a light chain constant region in which a heavy chain and light chain variable region is linked by a flexible linker. The short-chain antibody may refer to for example, U.S. Pat. No. 5,260,203, and this is disclosed herein by reference.

Herein, "domain antibody (dAb)" is an immunologically functional immunoglobulin fragment comprising a variable region of heavy chain or a variable region of light chain only. In one embodiment, two or more of VH regions are linked by a covalent bond by a peptide linker, to form a bivalent domain antibody. Two VH regions of this bivalent domain antibody may target the same or different antigen.

Herein, "bivalent antigen-binding protein" or "bivalent antibody" comprises 2 antigen-binding sites. Two antigen-binding sites comprised in this bivalent antibody may have the same antigen specificity or may be a dual-specific antibody binding to different antigens separately.

Herein, "multi-specific antigen-binding protein" or "multi-specific antibody" is targeting two or more of antigens or epitopes.

Herein, "bispecific", "dual-specific" antigen-binding protein or antibody is a hybrid antigen-binding protein or antibody having 2 different antigen-binding sites. This bispecific antibody is one kind of multi-specific antigen-binding protein or multi-specific antibody, and it can be produced by known various methods, for example, methods such as fusion of hybridoma or linking of Fab' fragment. For example, Songsivilai and Lachmann, 1990, Clin. Exp. Immunol. 79:315-321; Kostelny et al., 1992, J. Immunol. 148:1547-1553, etc. may be referred. The 2 epitopes different each other to which 2 antigen-binding sites of the bispecific antigen-binding protein or antibody bind may be positioned on the same or different protein target.

Herein, the term "antigen" or "immunogen" means a molecule or a part of molecule which for example, an antigen-binding protein (for example, antibody or its immunologically functional antigen-binding fragment) can bind to, and can be used for production of an antibody which can bind to an antigen in an animal. The antigen may comprise one or more of epitopes which can interact with a different antibody or its fragment. In one embodiment, the antigen is an extracellular domain of 4-1BB protein.

Herein, "epitope" is a part of molecule which is bound by an antigen-binding protein or antibody or is recognized by them, and comprise any determining factor which can specifically bind to an antigen-binding protein, such as for example, an antibody or a T-cell receptor. The epitope may be sequential or unsequential, and for example, in a polypeptide sequence, it is not sequential each other, but in an aspect of molecule, like a conformational epitope, it may be an amino acid residue that is bound by one antigen-binding protein, but is positioned away each other. In one embodiment, the epitope comprises a three-dimensional structure similar to an epitope used for antibody production, but it may be a mimetic in an aspect that it can comprise no residue found in the epitope or can comprise some residues only. Commonly, the epitope is a protein, but it may be other kinds of materials such as a nucleic acid. The epitope determining factor may be a chemically active group formed on a surface by a molecule such as an amino acid, a sugar side chain, a phosphoryl group or a sulfonyl group, or may have specific three-dimensional structural properties and/or specific charge properties. Commonly, an antibody which is specific to a specific target antigen recognizes an epitope of a target antigen which is present in a complex of a protein and/or a polymer.

Herein, "therapeutic agent" means a molecule to be administered to a subject for a targeting therapeutic effect. The subject includes a non-human mammal, for example, primates, or a human. The example of the therapeutic agent includes a protein comprising a peptide and a polypeptide, a nucleic acid, an antibody or a small molecular compound. In other aspect, the therapeutic agent can be used as a therapeutic agent of related diseases such as cancer, by being bound to the antibody, or the antibody.

Herein, the term "treating" means alleviation or treatment of an injury, disease, or symptom of disease or morbid condition, including any objective or subjective parameters, including reduction, relief, alleviation of an injury, disease, or symptom of disease or condition, or making a patient better able to withstand an injury, disease, or symptom of disease or morbid condition, slowing the deteriorating rate of an injury, disease, or symptom of disease or morbid condition, or improving the quality of life of a patient mentally or physically. This treatment or improvement of an injury, disease, or symptom of disease or morbid condition may be judged on the basis of results of physical examination, examination of various indexes related to a disease and imaging examination.

Herein, "effective amount (dose)" commonly means an amount enough to reduce seriousness and/or occurrence frequency of symptoms due to a disease, particularly, a disease related to 4-1BB, remove symptoms due to a disease, particularly, a disease related to 4-1BB and/or a root cause of disease occurrence, or prevent occurrence of symptoms due to a disease, particularly, a disease related to 4-1BB and/or a root cause, and/or improve or correct damages due to a disease, particularly, a disease related to 4-1BB. In some embodiments, the effective dose is a therapeutic effective dose or a prophylactic effective dose. The "therapeutic or pharmaceutically effective dose" is an amount enough to treat a disease, particularly symptoms or conditions related to 4-1BB, or prevent, delay a disease, particularly symptoms or conditions related to 4-1BB, or reverse its progress. The "prophylactic effective dose" is an amount for prevent or delay occurrence or reoccurrence of a disease, particularly, a disease related to 4-1BB, or symptoms related to a disease, particularly, a disease related to 4-1BB, and reduce its probability. The complete therapeutic or prophylactic effect can be caused by several times of administration of dose, rather than by a single administration of dose. Therefore, the therapeutic or prophylactic effective dose may be delivered by once or more of administration.

4-1BB 4-1BB, which is also called as CD137, or TNFRSF9 (TNF Receptor Superfamily Member 9), is a member of TNF-receptor superfamily (TNFRSF) and is a co-stimulatory molecule which is expressed following the activation of immune cells, both innate and adaptive immune cells. 4-1BB plays important role in modulate the activity of various immune cells. As used herein, 4-1BB may be originated from a mammal, for example, *Homo sapiens* (human) (NCBI Accession No. NP_001552).

For example, the human 4-1BB protein (NP_001552.2) may be represented by the amino acid sequence (SEQ ID NO: 67), as follows:

1 mgnscyniva tlllvlnfer trslqdpcsn cpagtfcdnn rnqicspcpp nsfssaggqr
61 tcdicrqckg vfrtrkecss tsnaecdctp gfhclgagcs mceqdckqgq eltkkgckdc
121 cfgtfndqkr gicrpwtncs ldgksvlvng tkerdvvcgp spadl-spgas svtppapare
181 pghspqiisf flaltstall fllflltlrf svvkrgrkkl lyifkqpfmr pvqttqeedg
241 cscrfpeeee ggcel As described herein, the term "4-1BB" includes variants, isoforms, homologs, orthologs, and paralogs. For example, antibodies specific for a human 4-1BB protein may, in certain cases, cross-react with a 4-1BB protein from a species other than human. In other embodiments, the antibodies specific for a human 4-1BB protein may be completely specific for the human 4-1BB protein and may exhibit species or other types of cross-reactivity, or may cross-react with 4-1BB from certain other species but not all other species (e.g., cross-react with monkey 4-1BB, but not mouse 4-1BB). The term "human 4-1BB" refers to human sequence 4-1BB, such as the complete amino acid sequence of human 4-1BB having NCBI Accession No. NP_001552. The term "mouse 4-1BB" refers to mouse sequence 4-1BB, such as the complete amino acid sequence of mouse 4-1BB having NCBI Accession No. NP_033430.1. 4-1BB also can be known in the art as, for example, CD137. The human 4-1BB sequence in the disclosure may differ from human 4-1BB of NCBI Accession No. NP_001552 by having, e.g., conserved mutations or mutations in non-conserved regions and the 4-1BB in the disclosure has substantially the same biological function as the human 4-1BB of NCBI Accession No. NP_001552.

Anti-4-1BB Antibodies

As demonstrated in the experimental examples, the anti-4-1BB antibodies disclosure herein show 4-1BB binding abilities, binding abilities to 4-1BB which expressed on cell surface, and high 4-1BB binding affinities. In addition, as demonstrated in the experimental example, the anti-4-1BB antibody disclosure herein, for instance, when combined with anti-PD-L1 antibody disclosure herein, is capable of activation T cell. Furthermore, as demonstrated in the experimental example, the anti-4-1BB antibody disclosure herein increases in vivo antitumor effect.

These anti-4-1BB antibodies may be useful for therapeutic purposes such as treating various types of cancer, etc., and can also be used for diagnostic and prognostic purposes.

The present invention discloses an antibody specifically binding to an extracellular domain of 4-1BB protein, or its antigen-binding fragment. The antibody is a polypeptide comprising one or more of complementary determining regions or sites (CDR), as disclosed herein.

In some embodiments, a CDR is comprised in a "framework" region, and the framework orients a CDR(s) so that this CDR(s) can have appropriate antigen-binding properties.

The antibody specifically binds to a human and mouse-derived 4-1BB extracellular domain, and it can specifically bind to an isolated form of extracellular domain or an extracellular domain of 4-1BB expressed on a cell surface.

The antibody disclosed herein binds to 4-1BB, in particular, human 4-1BB and mouse 4-1BB. The antibody disclosed herein can specifically bind to an 4-1BB extracellular domain or 4-1BB expressed on a cell surface, derived from a human or mouse, and thereby it can be usefully used for target treatment of cancer targeting 4-1BB. For example, it can be used for treatment of a specific cancer, by combining the antibody and an anti-cancer agent. In addition, an on-target tox can be confirmed through a mouse experiment, since it binds to mouse 4-1BB, and in vivo efficacy can be confirmed through a syngeneic model using a mouse cancer cell line overexpressing mouse 4-1BB, and thereby it can be usefully used for development of various drugs related to 4-1BB.

In one embodiment, the antibody includes a monoclonal antibody, dual-specific antibody, double antibody, multi-specific antibody, multiple antibody, minibody, domain antibody, antibody mimetic (or synthetic antibody), chimeric antibody or antibody fusion (or antibody conjugate) and fragment thereof, but not limited thereto, and includes various forms of antibodies disclosed herein.

In one embodiment, the antibody fragment of the antibody disclosed herein may be Fab, Fab', F(ab')2, scFab, Fv, dsFv, scFV, scFV-Fc, minibody, diabody, scAb, or dAb.

In other embodiment, the antibody disclosed herein may consist of a polypeptide of only light chains or only heavy chains comprising variable regions disclosed in Table 2a and Table 2b.

One antibody disclosed herein shares a specific region or sequence with another antibody disclosed herein. In one embodiment, it may share a constant region of the antibody or antigen-binding fragment. In another embodiment, it may share an Fc region. In another embodiment, it may share a frame of variable region.

In one embodiment, the antibody has a typical structure of an antibody found in nature. Camelid animals produces an antibody consisting of a single heavy chain, but the structural unit of this antibody commonly comprises a tetrameric polypeptide, and the tetramer comprises two of one pair of polypeptide chain bodies consisting of different 2 polypeptide chains. In a typical antibody, the one pair of polypeptide chain body comprises one full-length light chain (about 25 kDa) and one full-length heavy chain (about 50 to 70 kDa). Each chain shows a characteristic folding pattern, and consists of several immunoglobulin domains, consisting of about 90 to 110 amino acids. These domains are basic units consisting of an antibody polypeptide. The amino-terminal part of each chain typically comprises a part called a variable region or V region that is a part recognizing an antigen. The carboxy-terminal part is conserved evolutionarily more than the amino-terminal, and it comprises a part called a constant region or C region. The human light chain is commonly classified as kappa (κ) and lambda (λ) light chains, and these comprise one variable region and one constant region, respectively. The heavy chain is typically classified as mu (μ), delta (δ), gamma (γ), alpha (α) or epsilon (ε) chain, and these are defined as IgM, IgD, IgG, IgA and IgE isotypes, respectively. IgG includes IgG1, IgG2, IgG3 and IgG4, but has unlimited numerous subtypes. IgM subtype includes IgM and IgM2. IgA subtype includes IgA1 and IgA2. In human, IgA and IgD isotypes comprise 4 heavy chains and 4 light chains; IgG and IgE isotypes comprise 2 heavy chains and 2 light chains, and IgM isotype comprises 5 heavy chains and 5 light chains. The heavy chain constant region typically shows an effector function, but comprises one or more domains. The number of heavy chain constant region domains becomes different depending of isotypes. IgG heavy chain, for example, comprises 3 C region domains known as CH1, CH2 and CH3, respectively. The antibody disclosed herein may be any one of these isotypes and subtypes. In one embodiment, the antibody is an IgG1, IgG2a, IgG2b, IgG3 or IgG4 subtype. In a further embodiment, the antibody of the present invention is an IgG1- or IgG2-type. In a further embodiment, the antibody of the present invention is an IgG1-type.

The heavy chain variable region and light chain variable region may be linked to at least a part of a human constant region. The selection of a constant region may be determined by whether the antibody-dependent cell-mediated cytotoxicity, antibody-dependent cell phagocytosis, and/or complement-dependent cytotoxicity is required partially. For example, human isotype IgG1 and IgG3 have complement-dependent cytotoxicity and human isotype IgG2 and IgG4 do not have this cytotoxicity. In addition, human IgG1 and IgG3 induce a cell-mediated effector function stronger than human IgG2 and IgG4. The light chain constant region may be lambda or kappa.

In one embodiment, the antibody may be a humanized or human antibody, and the heavy chain constant region may be an IgG1-, IgG2- IgG3- or IgG4-type. In a further embodiment, the antibody of the present invention is an IgG1- or IgG2-type.

In other embodiment, the antibody is a humanized or human antibody, and recognizes mouse 4-1BB specifically.

In full-length light chain and heavy chain, a variable region and a constant region are linked by "J" region that is about 12 or more of amino acids in length, and the heavy chain also comprises "D" region of about 10 or more of amino acids. Typically, a variable region of light chain/ heavy chain pair of an antibody forms an antigen-binding site.

A variable region of an immunoglobulin chain has the same overall structure commonly, and comprises a comparatively conserved framework region (FR) connected by 3 hypervariable regions called "complementary determining site or region or domain" or CDR (Complementary Determining Region). The CDR of a variable region derived from each chain consisting of heavy chain/light chain pair is arranged by a framework region typically, thereby forming a structure specifically binding to a specific epitope of a target protein (4-1BB). These factors of naturally occurring light chain and heavy chain regions are typically comprised from the N-terminal to the C-terminal in the following order: FR1, CDR1, FR2, CDR2, FR3, CDR3 and FR4. The position of amino acid sequences corresponding to each of them in the variable region may be determined by Kabat (Kabat et al., (1983) U.S. Dept. of Health and Human Services, "Sequences of Proteins of Immunological Interest"), Chothia (Chothia and Lesk, J. Mol. Biol. 196:901-917 (1987)) or a method related to OPAL library (Hye Young Yang et. al., 2009 Mol. Cells 27: 225). The CDRs determined by each definition may be a subset which is overlapped or that one comprises the other, when comparing each other. However, herein, all CDRs to be defined by each method are included in the scope of the present invention. Those skilled in the art will easily select a CDR sequence by each definition among them, when the sequence of variable region of an antibody is provided.

In an embodiment, the anti-4-1BB antibody or fragment thereof is capable of specificity to a human 4-1BB protein. The anti-4-1BB antibody or fragment thereof may comprise (i) a CDR-H1 comprising an amino acid sequence selected from the group consisting of SEQ ID NOS: 1, 2, and 3; (ii) a CDR-H2 comprising an amino acid sequence selected from the group consisting of SEQ ID NOS: 4, 5, and 6; (iii) a CDR-H3 comprising an amino acid sequence selected from the group consisting of SEQ ID NOS: 7, 8, 9, 10, and 11; (iv) a VL CDR1 comprising an amino acid sequence of SEQ ID NO: 12 or 13; (v) a VL CDR2 comprising an amino acid sequence of SEQ ID NO: 14 or 15; and (vi) a VL CDR3 comprising an amino acid sequence of SEQ ID NO: 16 or 17.

In a specific embodiment, the anti-4-1BB antibody or fragment thereof may comprise: (a) a CDR-H1 of SEQ ID NO: 1, a CDR-H2 of SEQ ID NO: 4, a CDR-H3 of SEQ ID NO: 7, a VL CDR1 of SEQ ID NO: 12, a VL CDR2 of SEQ ID NO: 14, and a VL CDR3 of SEQ ID NO: 16;

(b) a CDR-H1 of SEQ ID NO: 1, a CDR-H2 of SEQ ID NO: 4, a CDR-H3 of SEQ ID NO: 8, a VL CDR1 of SEQ ID NO: 12, a VL CDR2 of SEQ ID NO: 14, and a VL CDR3 of SEQ ID NO: 16;

(c) a CDR-H1 of SEQ ID NO: 1, a CDR-H2 of SEQ ID NO: 4, a CDR-H3 of SEQ ID NO: 9, a VL CDR1 of SEQ ID NO: 12, a VL CDR2 of SEQ ID NO: 14, and a VL CDR3 of SEQ ID NO: 16;

(d) a CDR-H1 of SEQ ID NO: 2, a CDR-H2 of SEQ ID NO: 5, a CDR-H3 of SEQ ID NO: 10, a VL CDR1 of SEQ ID NO: 12, a VL CDR2 of SEQ ID NO: 14, and a VL CDR3 of SEQ ID NO: 16; or (e) a CDR-H1 of SEQ ID NO: 3, a CDR-H2 of SEQ ID NO: 6, a CDR-H3 of SEQ ID NO: 11, a VL CDR1 of SEQ ID NO: 13, a VL CDR2 of SEQ ID NO: 15, and a VL CDR3 of SEQ ID NO: 17.

In a non-limiting embodiment, the anti-4-1BB antibody or an antigen-binding fragment thereof may comprise;

a polypeptide comprising an amino acid sequence of SEQ ID NO: 40 as a H-FR1;

a polypeptide comprising an amino acid sequence of SEQ ID NO: 41 as a H-FR2;

a polypeptide comprising an amino acid sequence of SEQ ID NO: 42, 43, 44, or 45 as a H-FR3;

a polypeptide comprising an amino acid sequence of SEQ ID NO: 46 as a H-FR4;

a polypeptide comprising an amino acid sequence of SEQ ID NO: 47, 48, or 49 as a L-FR1;

a polypeptide comprising an amino acid sequence of SEQ ID NO: 50 or 51 as a L-FR2;

a polypeptide comprising an amino acid sequence of SEQ ID NO: 52 or 53 as a L-FR3; and/or a polypeptide comprising an amino acid sequence of SEQ ID NO: 54 or 55 as a L-FR4.

In a non-limiting example, the anti-4-1BB antibody or fragment thereof may comprise:

(1) a heavy chain variable region comprising or consisting essentially of a polypeptide comprising an amino acid sequence selected from the group consisting of SEQ ID NOS: 18, 19, 20, 21, 22, 23, 39, 57, 58, 59, and 60, or a polypeptide having a sequence identity of at least 80%, at least 85%, at least 90%, at least 95%, at least 96%, at least 97%, at least 98%, or at least 99% to the above described amino acid sequences; and/or (2) a light chain variable region comprising or consisting essentially of a polypeptide comprising an amino acid sequence selected from the group consisting of SEQ ID NOS: 24, 25, 26, 61, and 62, or a polypeptide having a sequence identity of at least 80%, at least 85%, at least 90%, at least 95%, at least 96%, at least 97%, at least 98%, or at least 99% to the above described amino acid sequences. In a non-limiting example, the anti-4-1BB antibody may comprise:

(1) a heavy chain comprising or consisting essentially of a polypeptide comprising an amino acid sequence selected from the group consisting of SEQ ID NOS: 27, 28, 29, 30, 31, and 32, or a polypeptide having a sequence identity of at least 80%, at least 85%, at least 90%, at least 95%, at least 96%, at least 97%, at least 98%, or at least 99% to the above described amino acid sequences; and/or (2) a light chain comprising or consisting essentially of a polypeptide comprising an amino acid sequence selected from the group consisting of SEQ ID NOS: 33, 34, and 35, or a polypeptide having a sequence identity of at least 80%, at least 85%, at least 90%, at least 95%, at least 96%, at least 97%, at least 98%, or at least 99% to the above described amino acid sequences.

The antibodies of the disclosure are characterized by particular functional features or properties of the antibodies. For example, the antibodies specifically bind to human 4-1BB and may bind to 4-1BB from certain other species, e.g., monkey 4-1BB, e.g., cynomolgus monkey, rhesus monkey, but may not substantially bind to 4-1BB from certain other species, e.g., mouse 4-1BB. Preferably, an antibody of the disclosure binds to human 4-1BB with high affinity.

The binding of an antibody or its antigen-binding fragment of the disclosure to 4-1BB can be assessed using one or more techniques well established in the art. For example, in a preferred embodiment, an antibody can be tested by a flow cytometry assay in which the antibody is reacted with a cell line that expresses human 4-1BB, such as CHO cells that have been transfected to express 4-1BB, e.g., human 4-1BB, or monkey 4-1BB, e.g., rhesus or cynomolgus monkey or mouse 4-1BB on their cell surface. Other suitable cells for use in flow cytometry assays include anti-CD3-stimulated $CD4^+$ activated T cells, which express native 4-1BB. Still other suitable binding assays include ELISA assays, for example using a recombinant 4-1BB protein. Additionally, or alternatively, the binding of the antibody, including the binding kinetics (e.g., KD value) can be tested in Octet analysis. Preferred binding affinities of an antibody of the disclosure include those with a dissociation constant or KD of $1\times10^{-6}$ M or less, $1\times10^{-7}$ M or less, or $1\times10^{-8}$ M or less, for example, $1.01\times10^{-9}$ M or less.

Further, the antibodies of the disclosure, particularly when constructed in the form of bispecific antibody, has the ability to enhance immune cell proliferation, survival, secretion of cytokines and cytolytic activity CD8 T cells. In certain embodiments, a bispecific antibody comprising an antibody of the disclosure and an anti-PD-L1 antibody, binds to human 4-1BB and exhibits an ability to activate T cells. Other ability of the antibody to stimulate an immune response include the ability of the antibody to inhibit tumor growth, such as in an in vivo tumor graft model.

In some embodiments, the anti-4-1BB antibody or fragment thereof further comprises a heavy chain constant region (e.g., SEQ ID NO: 36), a light chain constant region (e.g., SEQ ID NO: 37 or 38), an Fc region, or the combination thereof. In some embodiments, the light chain constant region may be a kappa or lambda chain constant region. In some embodiments, the antibody is of an isotype of IgG, IgM, IgA, IgE or IgD, for example, human IgG, human IgM, human IgA, human IgE, or human IgD. In some embodiments, the isotype may be IgG, for example human IgG, such as, IgG1, IgG2, IgG3, or IgG4. In some embodiments, the fragment (antigen-binding fragment of the anti-PD-L1 antibody) may be any fragment comprising heavy chain CDRs and/or light chain CDRs of the antibody, and for example, it may be selected from the group consisting of Fab, Fab', F(ab')$_2$, Fd (comprising a heavy chain variable region and a CH1 domain), Fv (a heavy chain variable region and/or a light chain variable region), single-chain Fv (scFv; comprising or consisting essentially of a heavy chain variable region and a light chain variable region, in any order, and a peptide linker between the heavy chain variable region and the light chain variable region), single-chain antibodies, disulfide-linked Fvs (sdFv), and the like.

Without limitation, the anti-4-1BB antibody or fragment thereof is a chimeric antibody, a humanized antibody, or a fully human antibody. In one aspect, antibody or fragment thereof is not naturally occurring, or chemically or recombinantly synthesized.

Given that each of these antibodies can bind to 4-1BB such as human 4-1BB, the CDR sequences or the $V_H$ and $V_L$ sequences can be "mixed and matched" to create other anti-4-1BB binding molecules of the disclosure. Preferably, when the CDRs sequences or $V_H$ and $V_L$ chains are mixed and matched, for example, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

An embodiment can be a polynucleotide encoding the 4-1BB antibody in a bispecific antibody. An embodiment can be a polynucleotide encoding a heavy chain of the bispecific antibody in an IgG-scFv form. Other embodiment can be a polynucleotide encoding a light chain of the bispecific antibody in the IgG-scFv form.

The IgG-scFv form may refer to a kind of a bispecific antibody comprising a full-length IgG antibody targeting (binding to) one of the two antigens and a scFv fragment targeting (binding to) the other one, wherein the scFv is linked to a C-terminus and/or N-terminus of the full-length IgG antibody directly (without a peptide linker) or via a peptide linker.

In an embodiment, when the bispecific antibody in an IgG-scFv form comprises a full-length IgG antibody against a certain antigen named X and a scFv fragment against 4-1BB, the polynucleotide encoding a heavy chain of the bispecific antibody may encode a heavy chain of the full-length IgG antibody against X and a scFv fragment against 4-1BB that is linked to a C-terminus and/or N-terminus of the full-length IgG antibody directly or via a peptide linker; and the polynucleotide encoding a light chain of the bispecific antibody may encode a light chain of the full-length IgG antibody against X.

Figure 7:
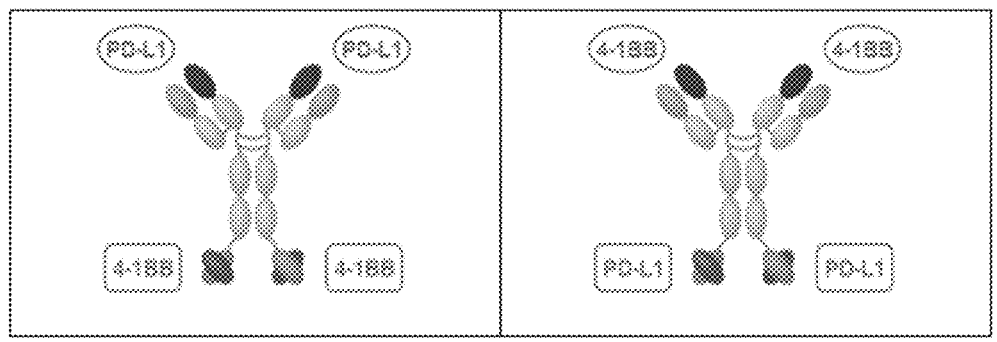
FIG. 7 is a schematic view of an anti-PD-L1/anti-4-1BB bispecific antibody.

In another embodiment, when the bispecific antibody in an IgG-scFv form comprises a full-length IgG antibody against 4-1BB and a scFv fragment against a certain antigen ("X"), the polynucleotide encoding a heavy chain of the bispecific antibody may encode a heavy chain of the full-length IgG antibody against 4-1BB and a scFv fragment against X that is linked to a C-terminus and/or N-terminus of the full-length IgG antibody directly or via a peptide linker; and the polynucleotide encoding a light chain of the bispecific antibody may encode a light chain of the full-length IgG antibody against 4-1BB. A representative embodiment (e.g., an anti-PD-L1/anti-4-1BB bispecific antibody) can be illustrated in FIG. 7.

The anti-4-1BB antibody or an antigen-binding fragment thereof may applied to treating and/or preventing a cancer and/or enhancing immune response. The enhancing immune response by the anti-4-1BB antibody or an antigen-binding fragment thereof may refer that the level of immune response, when the anti-4-1BB antibody or an antigen-binding fragment thereof is treated (or administered), is higher than that of the case when the anti-4-1BB antibody or an antigen-binding fragment thereof is not treated (or administered). The enhancing immune response may be 4-1BB signal activation, T-cell activation, or both of them.

In an embodiment, examples of the cancer may include blood cancer, lung cancer, stomach cancer, liver cancer, bone cancer, pancreatic cancer, skin cancer, head and neck cancer, skin melanoma, uterine cancer, ovarian cancer, rectal cancer, colorectal cancer, colon cancer, breast cancer, uterine sarcoma, fallopian tube carcinoma, endometrial carcinoma, uterine cervical carcinoma, vaginal carcinoma, vulva carcinoma, esophageal cancer, laryngeal cancer, small-intestine cancer, thyroid cancer, parathyroid cancer, soft-tissue sarcoma, urethral cancer, penile cancer, prostate cancer, chronic or acute leukemia, solid tumors in juvenile stage, differentiated lymphoma, bladder cancer, renal cancer, renal cell carcinoma, renal pelvic carcinoma, primary central nervous system lymphoma, spinal axis tumors, glioma, brain stem glioma, and pituitary adenoma, but are not limited thereto.

The effective ingredient such as the anti-4-1BB antibody, the antigen-binding fragment, etc. or the pharmaceutical composition may be administered orally or parenterally. For parenteral administration, intravenous injection, subcutaneous injection, intramuscular injection, intraperitoneal injection, endothelial administration, topical administration, intranasal administration, intrapulmonary administration, and intrarectal administration may be conducted. Since oral administration leads to digestion of proteins or peptides, an active ingredient in the compositions for oral administration may be coated or formulated to prevent digestion in the stomach. In addition, the composition may be administered using an optional device that enables an active ingredient to be delivered to target cells.

The pharmaceutically effective amount of the anti-4-1BB antibody or the antigen-binding fragment thereof may be prescribed in various amounts, depending on factors such as preparation (formulation) methods, method of administration, the patient's age, body weight, gender, pathologic conditions and diet, administration time, administration interval, administration route, excretion speed, and reaction sensitivity. For example, a daily dosage of the anti-4-1BB antibody or the antigen-binding fragment thereof may be within the range of 0.001 to 1000 mg/kg, particularly 0.01 to 100 mg/kg, more particularly 0.1 to 50 mg/kg, and even more particularly 0.1 to 20 mg/kg, but is not limited thereto. The daily dosage may be formulated into a single formulation in a unit dosage form or formulated in suitably divided dosage forms, or it may be manufactured to be contained in a multiple dosage container. The pharmaceutical composition may be administered in combination with other medications, and proper prescriptions may be made on the dose, the administration method, and kinds of the other medications, depending on patients' states.

The pharmaceutical composition may be formulated into a form of a solution in oil or an aqueous medium, a suspension, syrup, an emulsion, an extract, powder, granules, a tablet, or a capsule, and may further include a dispersing or a stabilizing agent for formulation.

Particularly, the pharmaceutical composition comprising the anti-4-1BB antibody or the antigen-binding fragment thereof may be formulated into an immunoliposome since it contains an antibody or an antigen-binding fragment. An antibody-containing liposome may be prepared using any of the methods widely known in the art. The immunoliposome may be a lipid composition including phosphatidylcholine, cholesterol, and polyethyleneglycol-derivatized phosphatidylethanolamine, and may be prepared by a reverse phase evaporation method. For example, Fab' fragments of an antibody may be conjugated to the liposome through a disulfide-exchange reaction.

The anti-4-1BB antibody or the antigen-binding fragment thereof, or the pharmaceutical composition may be administered to any subject, particularly a mammalian subject, for whom diagnosis, prognosis, or therapy is desired. Mammalian subjects may include humans, domestic animals, farm animals, and zoo, sport, or pet animals such as dogs, cats, guinea pigs, rabbits, rats, mice, horses, cattle, cows, and so on.

Another embodiment provides:
  a polynucleotide coding for the heavy-chain complementarity determining region, a polynucleotide coding for the light-chain complementarity determining region, or a combination thereof; a polynucleotide coding for the heavy-chain variable region, a polynucleotide coding for the light-chain variable region, or a combination thereof; or a polynucleotide coding for the heavy chain, a polynucleotide coding for the light chain, or a combination thereof, wherein the complementarity determining regions, the heavy- and light-chain variable regions, and the heavy and light chains are as described for the anti-4-1BB antibody above;
  a recombinant vector carrying the polynucleotides or a combination thereof; and/or
  a recombinant cell harboring the recombinant vector.

In one embodiment, the recombinant vector described above may contain polynucleotides coding respectively for a heavy-chain complementarity determining region and a light-chain complementarity determining region; for a heavy-chain variable region and a light-chain variable region; or for a heavy chain and a light chain in the anti-4-1BB antibody, in a single vector or in separate vectors carrying each of the polynucleotides.

The term "vector" refers to a means for expressing a target gene in a host cell, as exemplified by a plasmid vector, a cosmid vector, and a viral vector such as a bacteriophage vector, an adenovirus vector, a retrovirus vector, and an adeno-associated virus vector. The recombinant vector may be constructed from plasmids frequently used in the art (for example, pcDNA3.1, pcDNA3.4, pCHO1.0, pSC101, pGV1106, pACYC177, ColE1, pKT230, pME290, pBR322, pUC8/9, pUC6, pBD9, pHC79, pIJ61, pLAFR1, pHV14, pGEX series, pET series, and pUC19), phages (for example, λgt4λB, λ-Charon, λΔz1, and M13) or by manipulating viruses (for example, SV40, etc.).

In the recombinant vector, the polynucleotide may be operatively linked to a promoter. The term "operatively linked" is intended to pertain to a functional linkage between a nucleotide sequence of interest and an expression regulatory sequence (for example, a promoter sequence). When being "operatively linked", the regulatory element can control the transcription and/or translation of the nucleotide of interest.

The recombinant vector may be constructed typically as a cloning vector or an expression vector. For recombinant expression vectors, a vector generally available in the art for expressing a foreign protein in plant, animal, or microbial cells may be employed. Various methods well known in the art may be used for the construction of recombinant vectors.

For use in hosts, such as prokaryotic or eukaryotic cells, the recombinant vector may be constructed accordingly. For example, when a vector is constructed as an expression vector for use in a prokaryotic host, the vector typically includes a strong promoter for transcription (e.g., a pLκλ promoter, a CMV promoter, a trp promoter, a lac promoter, a tac promoter, a T7 promoter, etc.), a ribosomal binding site for initiating translation, and transcriptional/translational termination sequences. On the other hand, an expression vector for use in a eukaryotic host includes an origin of replication operable in a eukaryotic cell, such as an f1 origin of replication, an SV40 origin of replication, a pMB1 origin of replication, an adeno origin of replication, an AAV origin of replication, and a BBV origin of replication, but is not limited thereto. In addition, the expression vector typically includes a promoter derived from genomes of mammalian cells (for example, metallothionein promoter) or from mammalian viruses (for example, adenovirus late promoter, vaccinia virus 7.5K promoter, SV40 promoter, cytomegalovirus promoter, and tk promoter of HSV), and a polyadenylation sequence as a transcription termination sequence.

The recombinant cell may be prepared by introducing the recombinant vector into a suitable host cell. As long as it allows the sequential cloning and expression of the recombinant vector in a stable manner, any host cell known in the art may be employed in the present disclosure. Examples of the prokaryotic host cell available for the present disclosure include *E. coli*, *Bacillus* spp. such as *Bacillus subtilis* and *Bacillus thuringiensis*, and enterobacteriaceae strains such as *Salmonella typhimurium*, *Serratia marcescens* and various *Pseudomonas* species. Eukaryotic host cells that may be used for transformation may include, but are not limited to, *Saccharomyce cerevisiae*, insect cells, and animal cells, such as Sp2/0, CHO (Chinese hamster ovary), CHO-K1, CHO DG44, CHO-S, PER.C6, W138, BHK, COS-7, 293, HepG2, Huh7, 3T3, RIN, and MDCK.

The nucleic acid molecule or a recombinant vector carrying the same may be introduced (transfected) into a host cell using a method well known in the art. This transfection may be carried out using a CaCl2) or electroporation method when the host cell is prokaryotic. For eukaryotic host cells, the genetic introduction may be achieved using, but not limited to, microinjection, calcium phosphate precipitation, electroporation, liposome-mediated transfection, or particle bombardment.

To select a transformed host cell, advantage may be taken of a phenotype associated with a selection marker according to methods well known in the art. For example, when the selection marker is a gene conferring resistance to a certain antibiotic, the host cells may be grown in the presence of the antibiotic in a medium to select a transformant of interest.

Another aspect provides a method for production of an anti-4-1BB antibody or an antigen-binding fragment thereof, the method comprising a step of expressing the polynucleotide or the recombinant vector in a pertinent host cell. In one embodiment, the production method may comprise culturing a recombinant cell harboring the polynucleotide or the recombinant vector thereat, and optionally isolating and/or purifying the antibody from the culture medium.

EXAMPLES

Hereafter, the present invention will be described in detail by examples. The following examples are intended merely to illustrate the invention and are not construed to restrict the invention.

Example 1. Preparation of Anti-4-1BB Monoclonal Antibodies 1.1. Screening of Full Human Monoclonal Antibodies Against 4-1BB For panning of each of phage libraries (obtained from KBio Health and CUREBIO) against target molecules, A total of four rounds of panning were carried out using 4-1BB (NCBI Accession No. NP_001552.2; SEQ ID NO: 67) coated immunotubes.

Bacterial colonies from the 3 rounds of panning output were grown in SB-Carbenicilin in 96 deepwell plate until turbid, at which point $10^{11}$ pfu of VCSM13 helper phage was added to each well. After 1 h infection at 37° C. with gentle shaking (80 rpm), 70 μg/mL of kanamycin was added and the cells were cultured overnight at 30° C. with shaking at 200 rpm.

Next day, the plates were centrifuged and the supernatants containing the phages were added to 4-1BB antigen-coated ELISA plates blocked with 3% BSA in PBST. After 1 h incubation at room temperature, the plates were washed three times with PBST and anti M13 antibody was added. The plates were incubated for 1 h, washed three times with PBST, and the binding activity was measured using tetramethylbenzidine (TMB).

The 4-1BB specific binders were amplified for plasmid DNA sequencing. Ig light chain V genes (VL) and VH sequences were analyzed to identify unique sequences and determine sequence diversity.

While any type of IgG form can be prepared, sequences of the obtained 4-1BB specific antibodies in IgG4 form are summarized in Tables 2-9:

TABLE 2

| 41B01 | |
|---|---|
| 41B01 | Amino acid sequence (N'→C') |
| Heavy Chain | SEQ ID NO: 27 |
| Heavy Chain Variable Region (VH) | SEQ ID NO: 18 |
| H-CDR1 | SYDMS (SEQ ID NO: 1) |
| H-CDR2 | WISYSGGSIYYADSVKG (SEQ ID NO: 4) |
| H-CDR3 | DGQRNSMREFDY (SEQ ID NO: 7) |
| Light Chain | SEQ ID NO: 33 |
| Light Chain Variable Region (VL) | SEQ ID NO: 24 |

TABLE 2-continued

41B01

| 41B01 | Amino acid sequence (N'→C') |
|---|---|
| L-CDR1 | SGSSSNIGNNYVT (SEQ ID NO: 12) |
| L-CDR2 | ADSHRPS (SEQ ID NO: 14) |
| L-CDR3 | ATWDYSLSGYV (SEQ ID NO: 16) |

TABLE 3

41B01.01

| 41B01.01 | Amino acid sequence (N'→C') |
|---|---|
| Heavy Chain | SEQ ID NO: 28 |
| Heavy Chain Variable Region (VH) | SEQ ID NO: 19 |
| H-CDR1 | SYDMS (SEQ ID NO: 1) |
| H-CDR2 | WISYSGGSIYYADSVKG (SEQ ID NO: 4) |
| H-CDR3 | DAQRNSMREFDY (SEQ ID NO: 8) |
| Light Chain | SEQ ID NO: 33 |
| Light Chain Variable Region (VL) | SEQ ID NO: 24 |
| L-CDR1 | SGSSSNIGNNYVT (SEQ ID NO: 12) |
| L-CDR2 | ADSHRPS (SEQ ID NO: 14) |
| L-CDR3 | ATWDYSLSGYV (SEQ ID NO: 16) |

TABLE 4

41B01.02

| 41B01.02 | Amino acid sequence (N'→C') |
|---|---|
| Heavy Chain | SEQ ID NO: 29 |
| Heavy Chain Variable Region (VH) | SEQ ID NO: 20 |
| H-CDR1 | SYDMS (SEQ ID NO: 1) |
| H-CDR2 | WISYSGGSIYYADSVKG (SEQ ID NO: 4) |
| H-CDR3 | DAQRQSMREFDY (SEQ ID NO: 9) |
| Light Chain | SEQ ID NO: 33 |
| Light Chain Variable Region (VL) | SEQ ID NO: 24 |
| L-CDR1 | SGSSSNIGNNYVT (SEQ ID NO: 12) |
| L-CDR2 | ADSHRPS (SEQ ID NO: 14) |
| L-CDR3 | ATWDYSLSGYV (SEQ ID NO: 16) |

TABLE 5

41B01.03

| 41B01.03 | Amino acid sequence (N'→C') |
|---|---|
| Heavy Chain | SEQ ID NO: 28 |
| Heavy Chain Variable Region (VH) | SEQ ID NO: 19 |
| H-CDR1 | SYDMS (SEQ ID NO: 1) |
| H-CDR2 | WISYSGGSIYYADSVKG (SEQ ID NO: 4) |
| H-CDR3 | DAQRNSMREFDY (SEQ ID NO: 8) |
| Light Chain | SEQ ID NO: 34 |
| Light Chain Variable Region (VL) | SEQ ID NO: 25 |
| L-CDR1 | SGSSSNIGNNYVT (SEQ ID NO: 12) |
| L-CDR2 | ADSHRPS (SEQ ID NO: 14) |
| L-CDR3 | ATWDYSLSGYV (SEQ ID NO: 16) |

TABLE 6

41B01.04

| 41B01.04 | Amino acid sequence (N'→C') |
|---|---|
| Heavy Chain | SEQ ID NO: 29 |
| Heavy Chain Variable Region (VH) | SEQ ID NO: 20 |
| H-CDR1 | SYDMS (SEQ ID NO: 1) |
| H-CDR2 | WISYSGGSIYYADSVKG (SEQ ID NO: 4) |
| H-CDR3 | DAQRQSMREFDY (SEQ ID NO: 9) |
| Light Chain | SEQ ID NO: 34 |
| Light Chain Variable Region (VL) | SEQ ID NO: 25 |
| L-CDR1 | SGSSSNIGNNYVT (SEQ ID NO: 12) |
| L-CDR2 | ADSHRPS (SEQ ID NO: 14) |
| L-CDR3 | ATWDYSLSGYV (SEQ ID NO: 16) |

TABLE 7

41B02

| 41B02 | Amino acid sequence (N'→C') |
|---|---|
| Heavy Chain | SEQ ID NO: 30 |
| Heavy Chain Variable Region (VH) | SEQ ID NO: 21 |
| H-CDR1 | GYDMS (SEQ ID NO: 2) |
| H-CDR2 | VIYPDDGNTYYADSVKG (SEQ ID NO: 5) |
| H-CDR3 | HGGQKPTTKSSSAYGMDG (SEQ ID NO: 10) |

TABLE 7-continued

41B02

| 41B02 | Amino acid sequence (N'→C') |
|---|---|
| Light Chain | SEQ ID NO: 33 |
| Light Chain Variable Region (VL) | SEQ ID NO: 24 |
| L-CDR1 | SGSSSNIGNNYVT (SEQ ID NO: 12) |
| L-CDR2 | ADSHRPS (SEQ ID NO: 14) |
| L-CDR3 | ATWDYSLSGYV (SEQ ID NO: 16) |

TABLE 8

41B02.01

| 41B02.01 | Amino acid sequence (N'→C') |
|---|---|
| Heavy Chain | SEQ ID NO: 31 |
| Heavy Chain Variable Region (VH) | SEQ ID NO: 22 |
| H-CDR1 | GYDMS (SEQ ID NO: 2) |
| H-CDR2 | VIYPDDGNTYYADSVKG (SEQ ID NO: 5) |
| H-CDR3 | HGGQKPTTKSSSAYGMDG (SEQ ID NO: 10) |
| Light Chain | SEQ ID NO: 34 |
| Light Chain Variable Region (VL) | SEQ ID NO: 25 |
| L-CDR1 | SGSSSNIGNNYVT (SEQ ID NO: 12) |
| L-CDR2 | ADSHRPS (SEQ ID NO: 14) |
| L-CDR3 | ATWDYSLSGYV (SEQ ID NO: 16) |

TABLE 9

41B03

| 41B03 | Sequence |
|---|---|
| Heavy Chain | SEQ ID NO: 32 |
| Heavy Chain Variable Region (VH) | SEQ ID NO: 23 |
| CDR-H1 | SNVMN (SEQ ID NO: 3) |
| CDR-H2 | EISHSGSTNYNPSLKS (SEQ ID NO: 6) |
| CDR-H3 | GAGNLGY (SEQ ID NO: 11) |
| Light Chain | SEQ ID NO: 35 |
| Light Chain Variable Region (VL) | SEQ ID NO: 26 |
| CDR-L1 | QASQDISNYLN (SEQ ID NO: 13) |
| CDR-L2 | GASSRAT (SEQ ID NO: 15) |
| CDR-L3 | QQYNSYPIT (SEQ ID NO: 17) |

1.2. Preparation of scFv Antibodies Against 4-1BB

Anti-4-1BB scFv antibodies with a structure of (N')-VL-linker-VH-(C') were prepared using the variable regions of the full human monoclonal antibodies against 4-1BB shown in the tables of Example 1.1, wherein the amino acid residue "G" at the position 44 of a heavy chain variable region was substituted with "C", and the amino acid residue "G" at the position 103 of a light chain variable region was substituted with "C". Such amino acid substitution from "G" to "C" in scFv can contribute to increase in stabilities of bispecific antibodies comprising the scFv as one target-specific moiety. The amino acid sequences of the prepared anti-4-1BB scFvs were illustrated in the following tables, while skilled persons in the art may apply changes or modifications of amino acid sequences in the following embodiments to meet specific purposes, including applying various types of peptide linkers such as (GGGGS) 2 (SEQ ID NO: 68), (GGGGS) 3 (SEQ ID NO: 56), (GGGGS) 4 (SEQ ID NO: 66), or (GS) 9 (SEQ ID NO: 69).

Sequences of the obtained 4-1BB specific antibodies in scFv form are summarized in Tables 10-15:

TABLE 10

41B01 (scFv)

| | Amino acid sequence (N'→C') |
|---|---|
| Light chain variable region (VL) | SEQ ID NO: 61 |
| Linker | SEQ ID NO: 56 |
| Heavy chain variable region (VH) | SEQ ID NO: 57 |

TABLE 11

41B01.01 (scFv)

| | Amino acid sequence (N'→C') |
|---|---|
| Light chain variable region (VL) | SEQ ID NO: 61 |
| Linker | SEQ ID NO: 56 |
| Heavy chain variable region (VH) | SEQ ID NO: 58 |

TABLE 12

41B01.03 (scFv)

| | Amino acid sequence (N'→C') |
|---|---|
| Light chain variable region (VL) | SEQ ID NO: 62 |
| Linker | SEQ ID NO: 56 |
| Heavy chain variable region (VH) | SEQ ID NO: 58 |

TABLE 13

41B01.04 (scFv)

| | Amino acid sequence (N'→C') |
|---|---|
| Light chain variable region (VL) | SEQ ID NO: 62 |
| Linker | SEQ ID NO: 56 |
| Heavy chain variable region (VH) | SEQ ID NO: 39 |

TABLE 14

41B02 (scFv)

| | Amino acid sequence (N'→C') |
|---|---|
| Light chain variable region (VL) | SEQ ID NO: 61 |
| Linker | SEQ ID NO: 56 |
| Heavy chain variable region (VH) | SEQ ID NO: 59 |

TABLE 15

41B02.01 (scFv)

| | Amino acid sequence (N'→C') |
|---|---|
| Light chain variable region (VL) | SEQ ID NO: 62 |
| Linker | SEQ ID NO: 56 |
| Heavy chain variable region (VH) | SEQ ID NO: 60 |

1.4. Preparation of scFv Antibodies Against 4-1BB in the Form of Bispecific Antibody As a representative example of a bispecific antibody, PD-L1×4-1BB bispecific antibodies consisting of heavy components and light components as follows, were prepared:
(1) Heavy Components (N'→C')
  1) heavy chain of anti-PD-L1 antibody: SEQ ID NO: 63 or SEQ ID NO: 65,
  2) linker: SEQ ID NO: 66 (GGGGSGGGGSGGGGS), and
  3) anti-4-1BB scFv, 41B01 (scFv) (Table 10), 41B01.01 (scFv) (Table 11), 41B01.02 (scFv), 41B01.03 (scFv) (Table 12), or 41B01.04 (scFv) (Table 13), prepared in Example 1.2; and
(2) Light Components (N'→C')
  Light chain of anti-PD-L1 antibody: SEQ ID NO: 64.

Figure 1B:
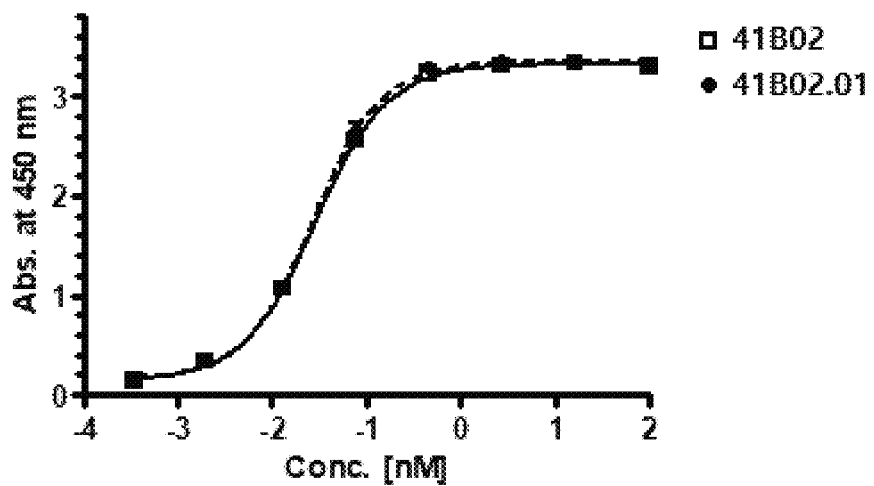
Figure 1C:
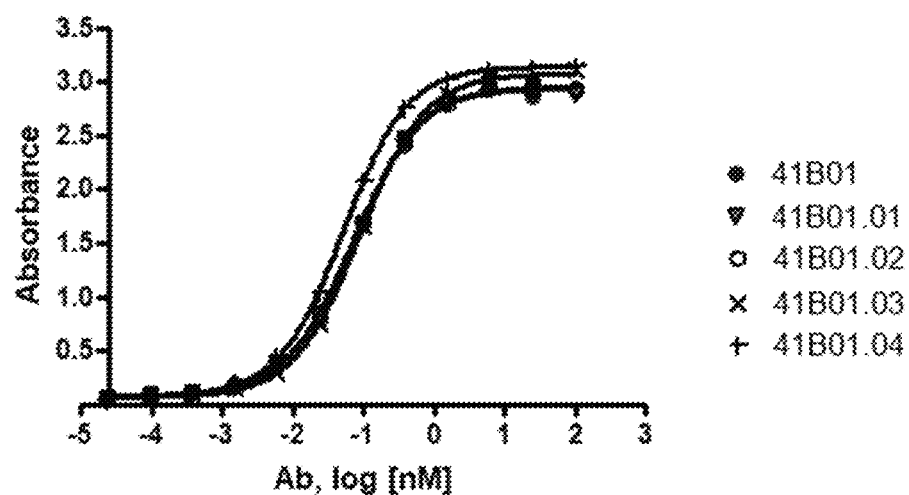

1.5. Antigen Binding Abilities of Anti-4-1BB Antibodies to Human 4-1BB (1) Antigen Binding Measured by ELISA To evaluate the antigen binding activity, the antibody candidates were subjected to ELISA test. Briefly, microtiter plates were coated with human 4-1BB-Fc protein at 0.1 µg/ml in PBS, 100 µl/well at 4° C. overnight, then blocked with 100 µl/well of 5% BSA. Serial dilutions of antibodies obtained in Example 1.1 were added to each well and incubated for 1-2 hours at RT. The plates were washed with PBS/TWEEN® and then incubated with goat-anti-human IgG antibody conjugated with Horse Radish Peroxidase (HRP) for 1 hour at RT. After washing, the plates were developed with TMB substrate and analyzed by spectrophotometer at OD 450-630 nm. The obtained results are shown in FIGS. 1A-1C. As shown in FIGS. 1A, 1B, and 1C, the anti-4-1BB antibodies tested showed high 4-1BB binding abilities.

(2) Cell Binding Measured by FACS

Figure 2:
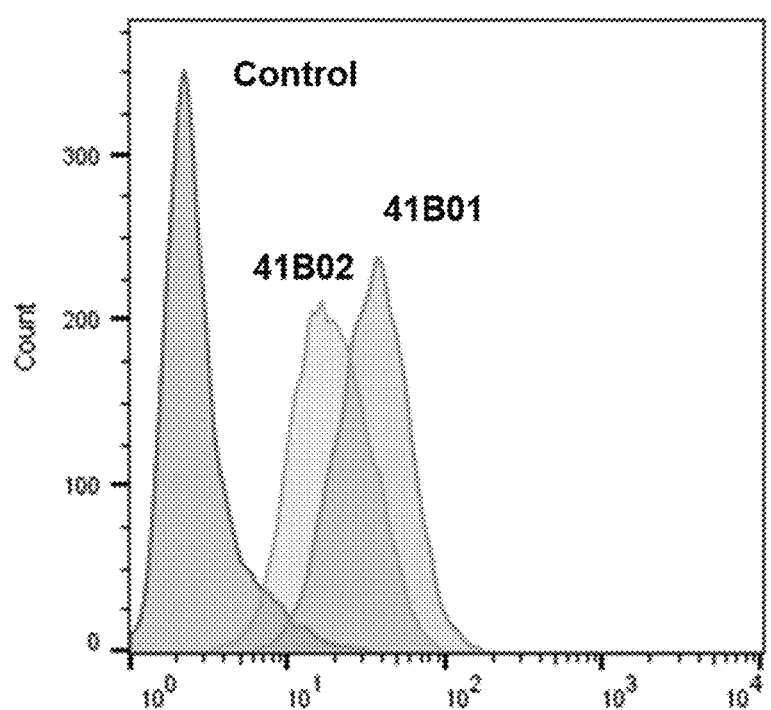
FIG. 2 is the result of measurement (FACS) of the binding capacity to the 4-1BB antigen of the anti-4-1BB antibody prepared according to one embodiment of the present invention. It shows that each anti-4-1BB monoclonal antibody specifically binds to the 4-1BB expressed on the cell surface.

To evaluate the antigen binding property, the antibody candidates were analyzed for its binding to mammalian expressed 4-1BB by FACS. Briefly, 4-1BB-Jurkat cells were incubated with antibodies (41B01 and 41B02). After wash by FACS buffer (1% BSA in PBS), the FITC-anti-human IgG antibody was added to each well and incubated at 4° C. for 1 hour. The MFI of FITC was evaluated by FACS Caliber. As shown in FIG. 2, the anti-4-1BB antibodies tested show binding abilities to 4-1BB which expressed on cell surface and can efficiently bind to 4-1BB expressed on mammalian cells.

As shown in FIG. 2, the anti-4-1BB antibodies tested show binding abilities to 4-1BB which expressed on cell surface.

(3) Protein Kinetic for 4-1BB

To explore the binding kinetics of the humanized antibody, this example performed the affinity ranking by using Octet Red 96. As shown in Table 16 below, the anti-4-1BB antibodies tested show high 4-1BB binding affinities.

TABLE 16

4-1BB Affinity Result of OCTET

| Antibody | KD (M) | kon(1/Ms) | kdis(1/s) | chi | $R^2$ |
|---|---|---|---|---|---|
| 41B01 | 1.80E−10 | 6.58E+05 | 1.19E−04 | 0.0392 | 0.9987 |
| 41B02 | 1.01E−09 | 5.95E+05 | 6.03E−04 | 0.0525 | 0.9973 |
| 41B03 | 7.90E−10 | 7.55E+05 | 5.97E−04 | 0.1213 | 0.9951 |

(4) Epitope Mapping

Epitope mapping was performed to identify the unique epitope of the 4-1BB antibodies. Almost all surface residues of 4-1BB (NCBI Accession No. NP_001552.2) were mutated screened by high-throughput flowcytometry to map epitope by Ranomics (Toronto, CA). A GFP tag was fused to the C-terminus of 4-1BB, and each surface residue of the extracellular domain (24-186) of 4-1BB was mutated to Arg. If the residue is Arg, it was mutated to Glu. The mutated plasmid was pooled into a library and transfected to the HEK293 cell line. The resulting cell line was sorted against GFP and/or 41B01/41B02 binding. The population of each mutant in the sorted cell pool was analyzed by RNAseq. If a mutant shows a higher count in the GFP pool than the GFP/anti-4-1BB pool, the mutated site was considered as an epitope. The epitope residues are listed in Table 17:

TABLE 17

| clone | Epitope residues of 4-1BB (NCBI Accession No. NP_001552.2) | Domain |
|---|---|---|
| 41B01 | Phe125, Gly150, Arg154, Asp155, Val157 | CRD4 |
| 41B02 | Trp136, Thr137, Leu147, Gly150, Arg154 | CRD4 |

Figure 8A:
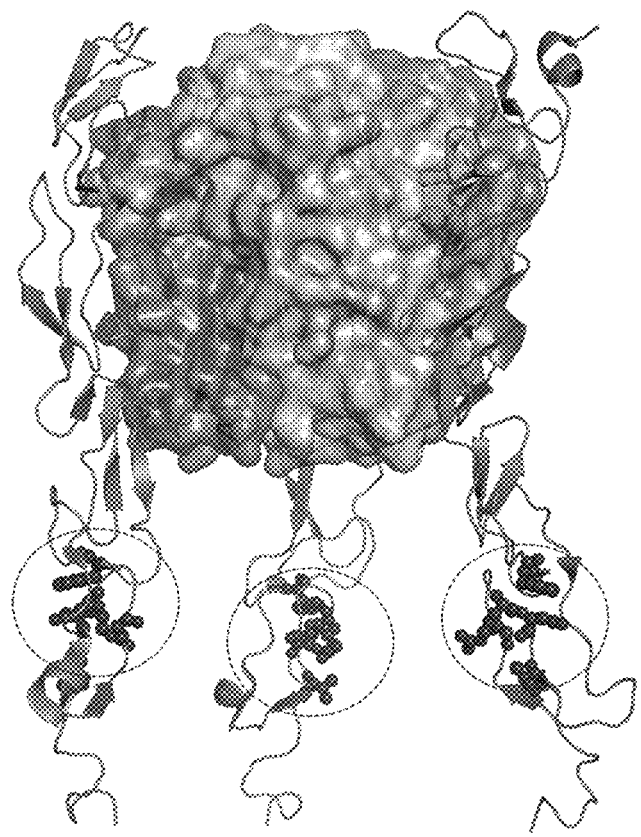
FIG. 8A is a schematic view showing binding sites of an anti-4-1BB antibody (41B01) on 4-1BB.
Figure 8B:
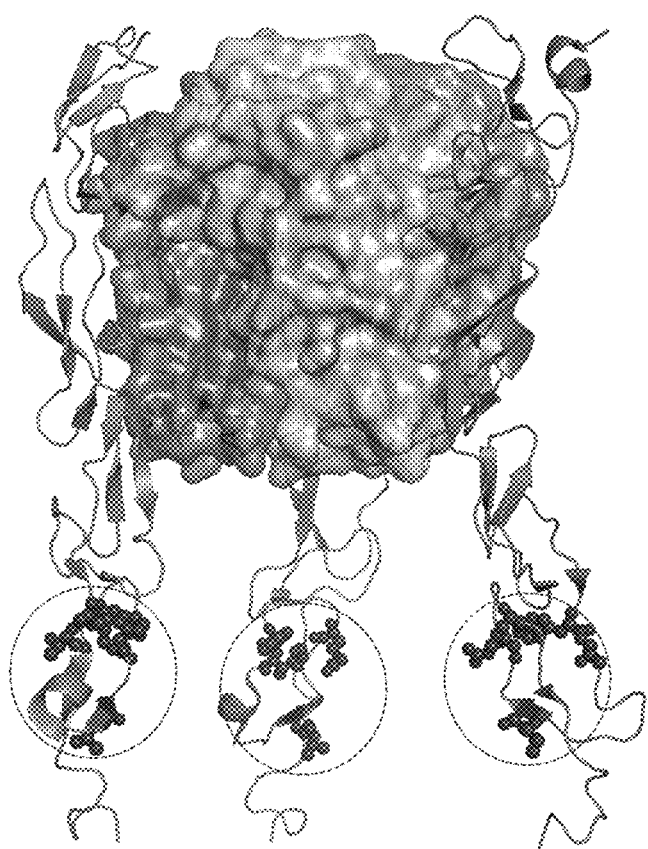
FIG. 8B is a schematic view showing binding sites of an anti-4-1BB antibody (41B02) on 4-1BB.

FIGS. 8A and 8B show the epitopes of the 41B01 clone and 41B02 clone. In the figures, 4-1BB protein is shown in ribbon as bound with 4-1BB ligand in molecular surface representation (PDB ID:6MGP). The identified epitope residues within 4-1BB for anti-4-1BB antibodies are shown in spheres. As shown in the figures, 41B01 and 41B02 bind to the epitopes within CDR4 of 4-1BB, which are far from the binding site of 4-1BBL within 4-1BB. As such, 41B01 and 41B02 do not compete with 4-1BBL.

These observations are in agreement with the finding in Example 1.5 (5) competition assay that 41B01 and 41B02 do not compete with 4-1BBL, while utomilulumab competes with 4-1BBL. Utomilulumab also competes with 41B01 or 41B02. Because utomilumab binds to an epitope within CRD3~4 (87-118) of 4-1BB, the binding site of utomilumab within 4-1BB is close to and overlaps with the binding site of 4-1BBL, 41B01, or 41B02.

(5) Competition Assay

Competition assay was performed to test if the 4-1BB antibodies have unique epitope.

A 96 well black microplate (greiner bio one) was installed in a biosensor tray case, then 200 µL of 1× Kinetic Buffer (1×KB) was added in 8 wells respectively. 8 Ni-NTA biosensors (ForteBio, USA) were hydrated by soaking in the wells with buffer for 10 min. Analytes (41B01, 41B02, Urelumab, Utomilumab, Recombinant Human 41BB Ligand) were diluted using 1×KB to the concentration of 100 nM. Recombinant Human 41BB-His tag protein (Sino Biological, 10041-H08H) was diluted with 1×KB buffer to the concentration of 2 μg/mL which was then used for antigen fixation on the biosensor.

The experiment was performed by sequential association steps of two analytes based on the Table 18. 1×KB was added to a new 96 well black microplate according to the octet program template. Biosensors are soaked in the 1×KB 200 μL to generate Baseline1, followed by placing biosensors to 200 μL of the antigen, Recombinant Human 41BB His tag protein (2 μg/mL) to fix antigen on the biosensor. After re-hydrating biosensors in 1×KB 200 μL (Baseline2), first analyte (200 μL) was associated with the antigen on the biosensors. Subsequently, second analyte (200 μL) was associated with the molecules on the biosensors. The temperature of the experimental plate was controlled with 30° C. After finishing the experiment, cross-competition between the first and second analytes was evaluated with the Octet Analysis 9.0 software.

TABLE 18

List of Analytes

| Run number | First Analyte | Second Analyte |
| --- | --- | --- |
| 1 | Urelumab | Urelumab |
| 2 | Urelumab | 41B02 |
| 3 | 41B01 | Urelumab |
| 4 | Urelumab | 41B02 |
| 5 | 41B02 | Urelumab |
| 6 | Utomilumab | Utomilumab |
| 7 | Utomilumab | 41B01 |
| 8 | 41B01 | Utomilumab |
| 9 | Utomilumab | 41B02 |
| 10 | 41B02 | Utomilumab |
| 11 | 41B01 | 41B01 |
| 12 | 41B01 | 41B02 |
| 13 | 41B02 | 41B01 |
| 14 | 41B02 | 41B02 |
| 15 | Recombinant Human 41BB-Ligand | Recombinant Human 41BB-Ligand |
| 16 | Recombinant Human 41BB-Ligand | 41B01 |
| 17 | 41B01 | Recombinant Human 41BB-Ligand |

The obtained results are shown in FIGS. 9A-12C.

Figure 9A:
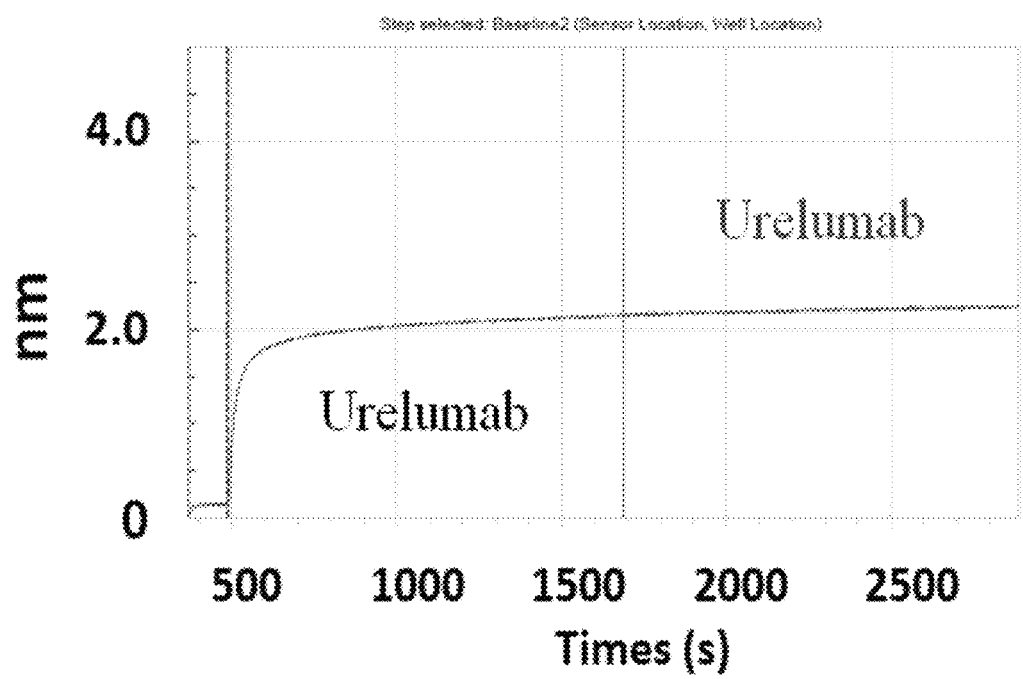
FIGS. 9A-9E show cross-competition between Urelumab and candidates (41B01 and 41B02).
Figure 9B:
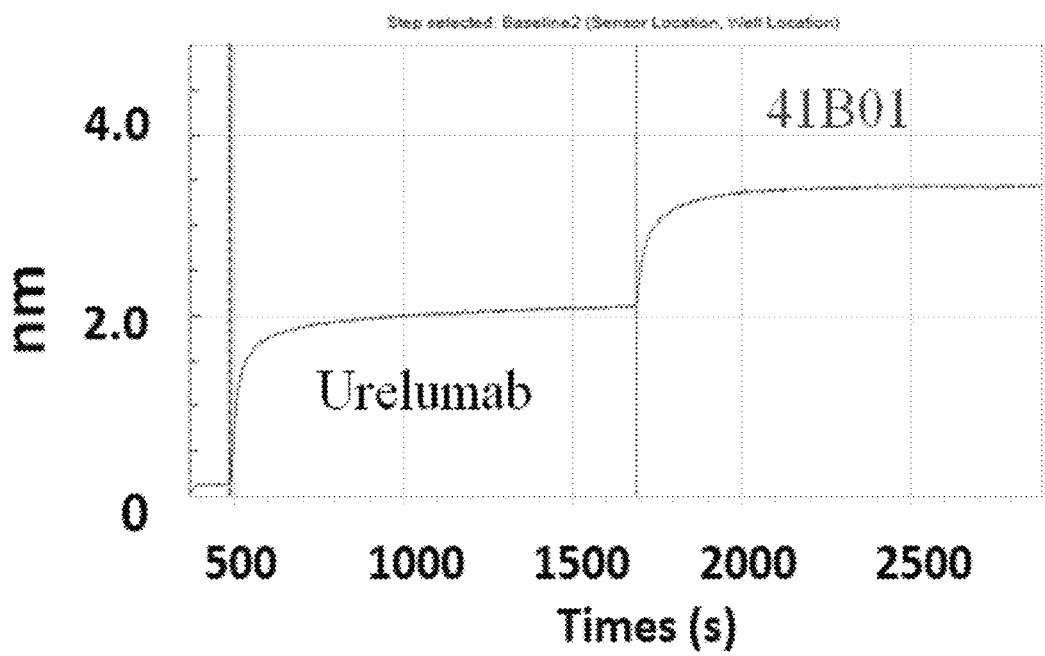
Figure 9C:
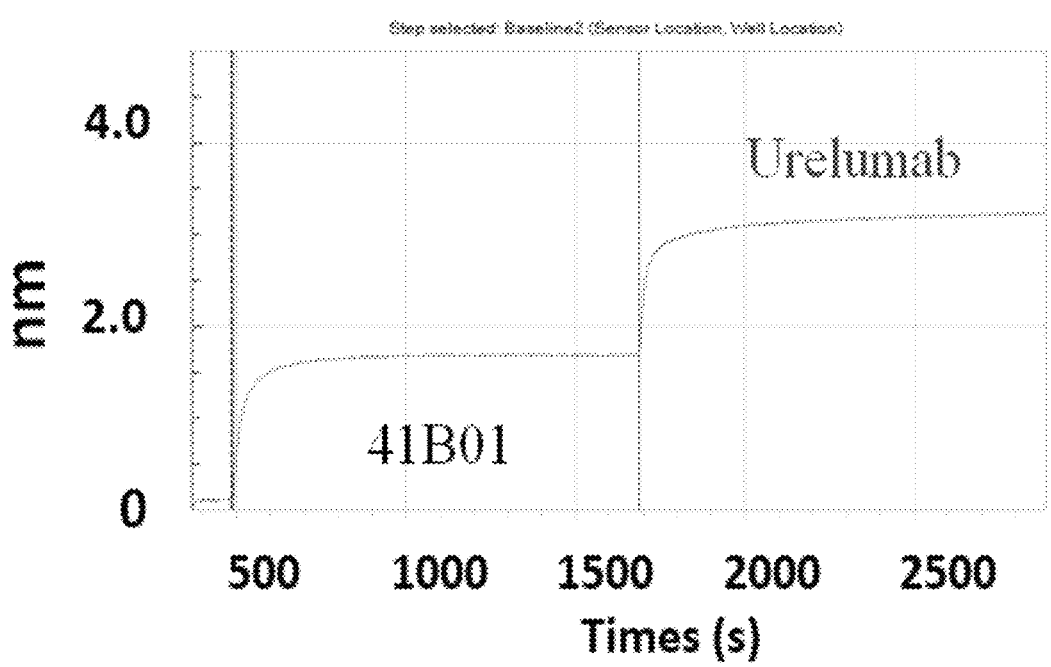
Figure 9D:
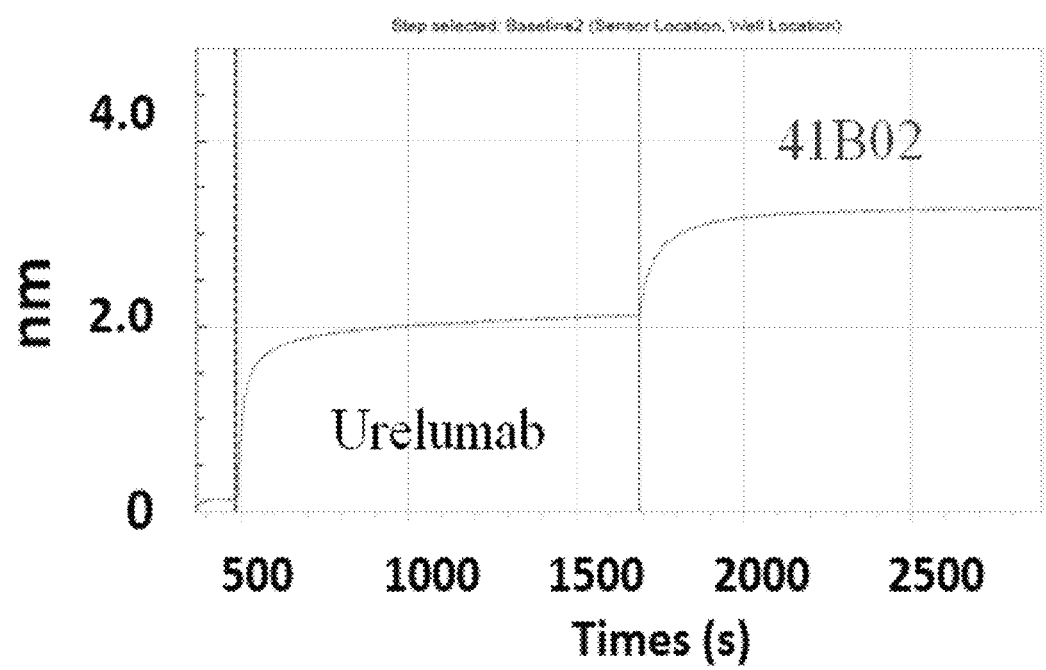
Figure 9E:
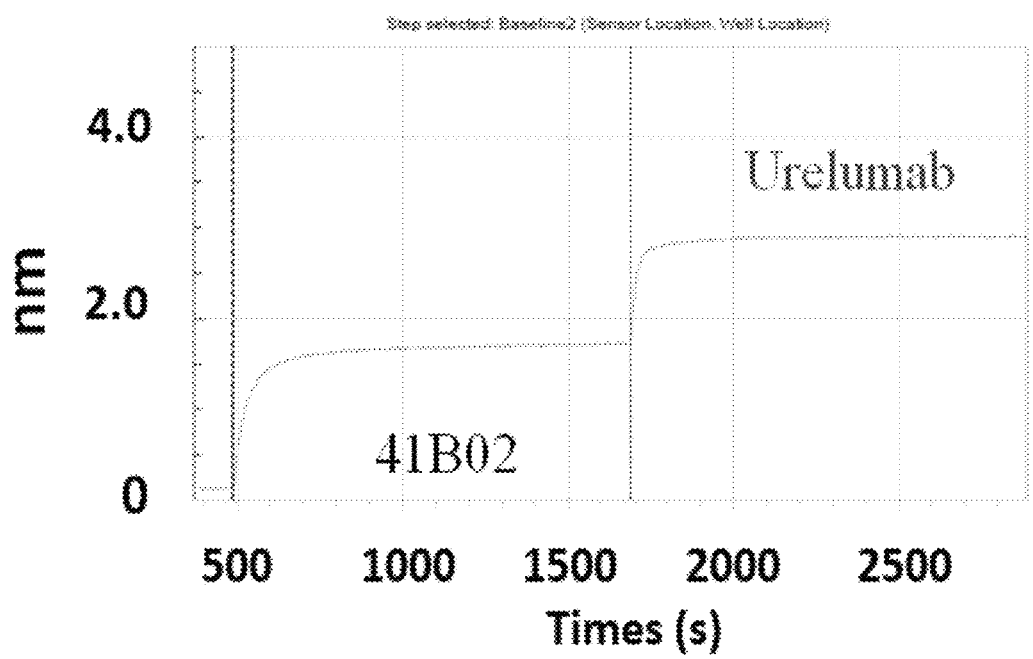

FIGS. 9A-9E show cross-competition between Urelumab and candidates (41B01 and 41B02). Competition assay was performed between Urelumab and two candidates (41B01 and 41B02). Recombinant human 41BB-His tag protein was firstly fixed on the biosensor. Then primary and secondary antibodies were sequentially associated with the biosensor to detect binding competition between two antibodies. Overall, no binding competition was not observed between Urelumab and two candidates indicating that each antibody has unique epitope. FIG. 9A shows results of self-binding of Urelumab (control), FIG. 9B shows results of Urelumab as a $1^{st}$ antibody and 41B01 as a $2^{nd}$ antibody, FIG. 9C shows results of 41B01 as a $1^{st}$ antibody and Urelumab as a $2^{nd}$ antibody, FIG. 9D shows results of Urelumab as a $1^{st}$ antibody and 41B02 as a $2^{nd}$ antibody, and FIG. 9E shows results of 41B02 as a $1^{st}$ antibody and Urelumab as a $2^{nd}$ antibody.

Figure 10A:
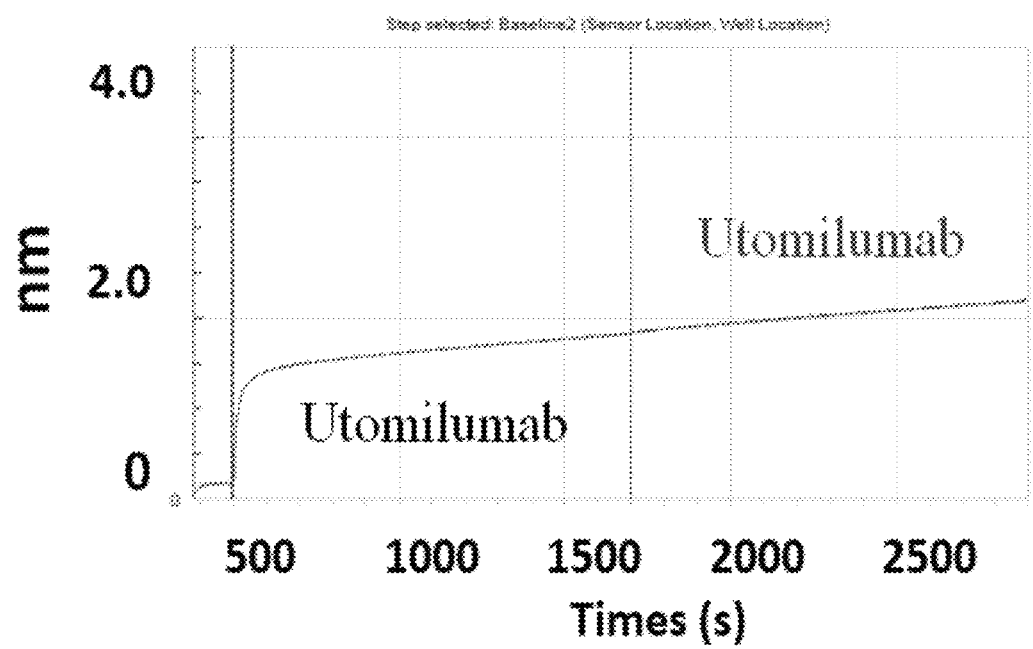
FIGS. 10A-10E show cross-competition between Utomilumab and candidates (41B01 and 41B02).
Figure 10B:
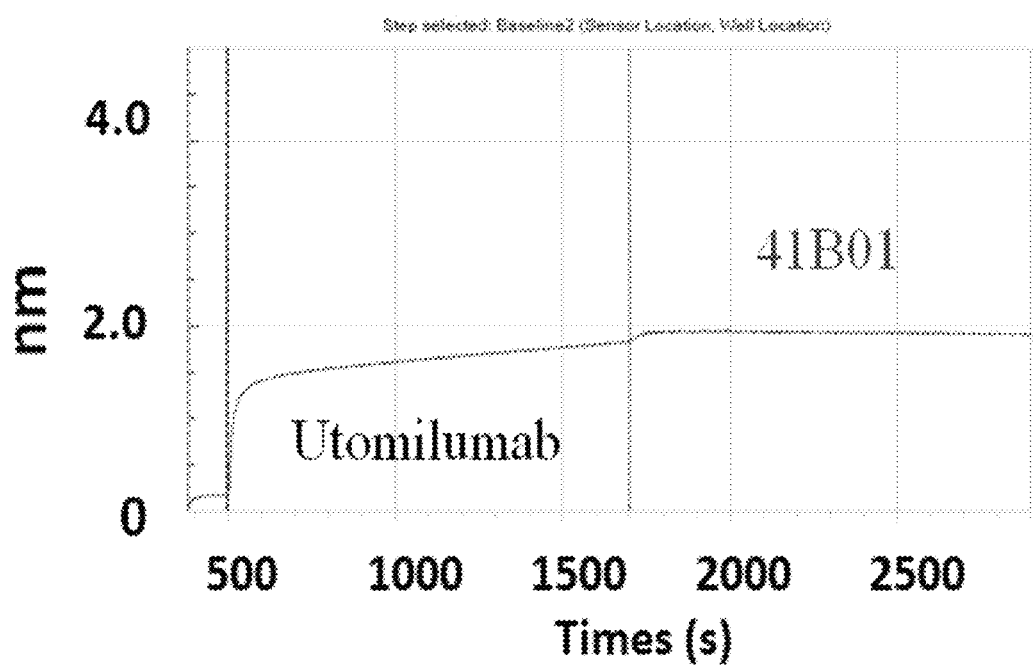
Figure 10C:
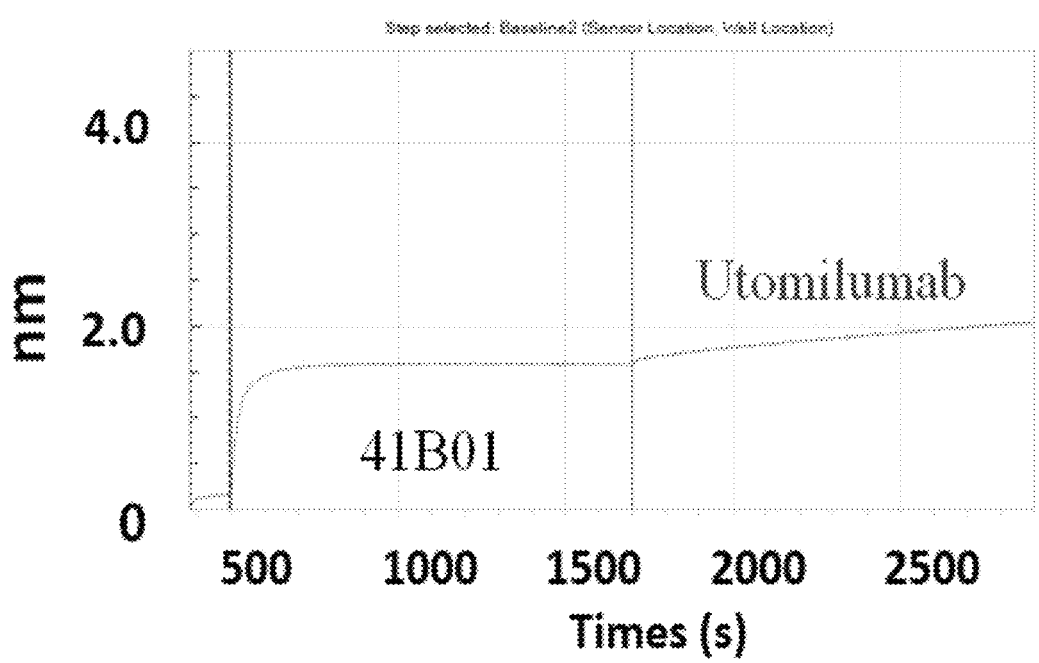
Figure 10D:
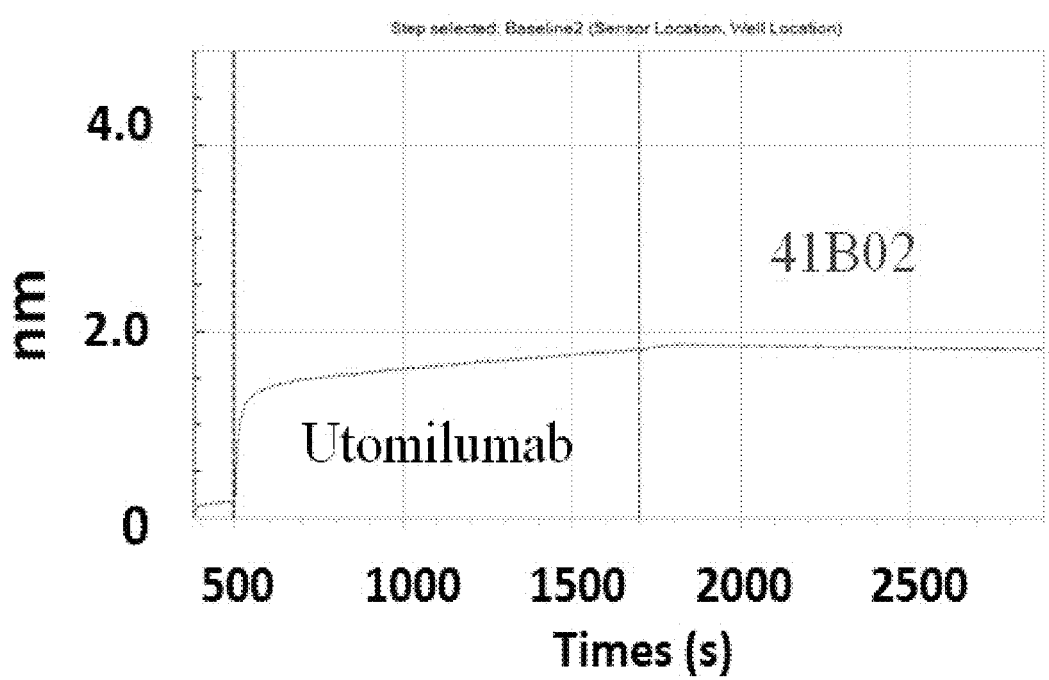
Figure 10E:
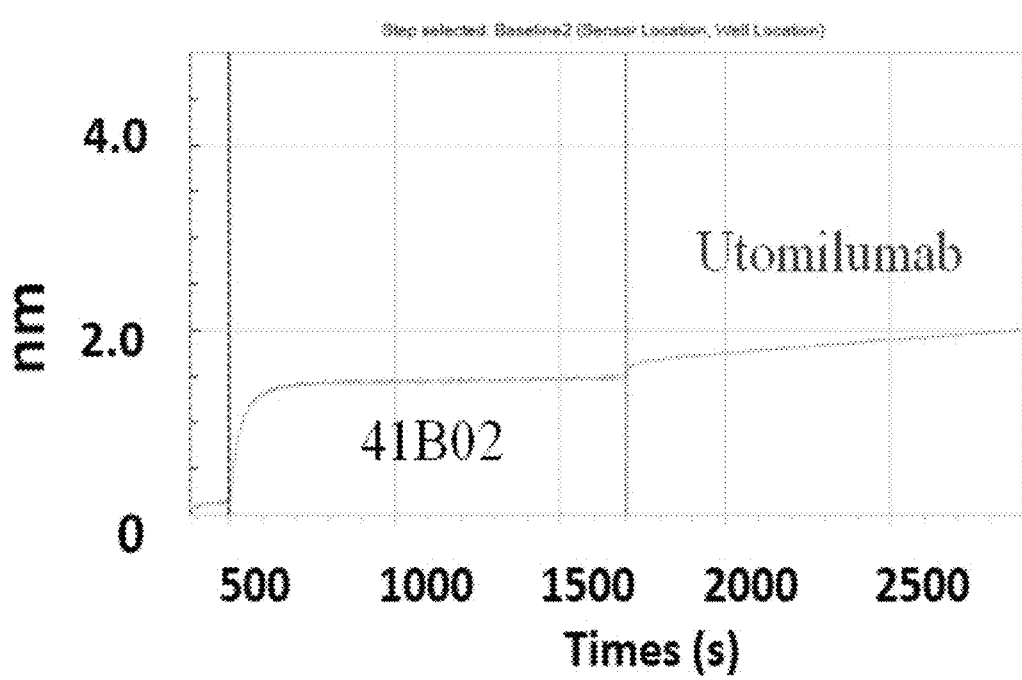

FIGS. 10A-10E show cross-competition between Utomilumab and candidates (41B01 and 41B02). Competition assay was performed between Utomilumab and two candidates (41B01 and 41B02). Recombinant human 41BB-His tag protein was firstly fixed on the biosensor. Then primary and secondary antibodies were sequentially associated with the biosensor to detect binding competition between two antibodies. Overall, no binding competition was not observed between Utomilumab and two candidates, indicating that each antibody has unique epitope. FIG. 10A shows results of self-binding of Utomilumab (control), FIG. 10B shows results of Utomilumab as a $1^{st}$ antibody and 41B01 as a $2^{nd}$ antibody, FIG. 10C shows results of 41B01 as a 1st antibody and Utomilumab as a $2^{nd}$ antibody, FIG. 10D shows results of Utomilumab as a 1st antibody and 41B02 as a $2^{nd}$ antibody, and FIG. 10E shows results of 41B02 as a $1^{st}$ antibody and Utomilumab as a $2^{nd}$ antibody.

Figure 11A:
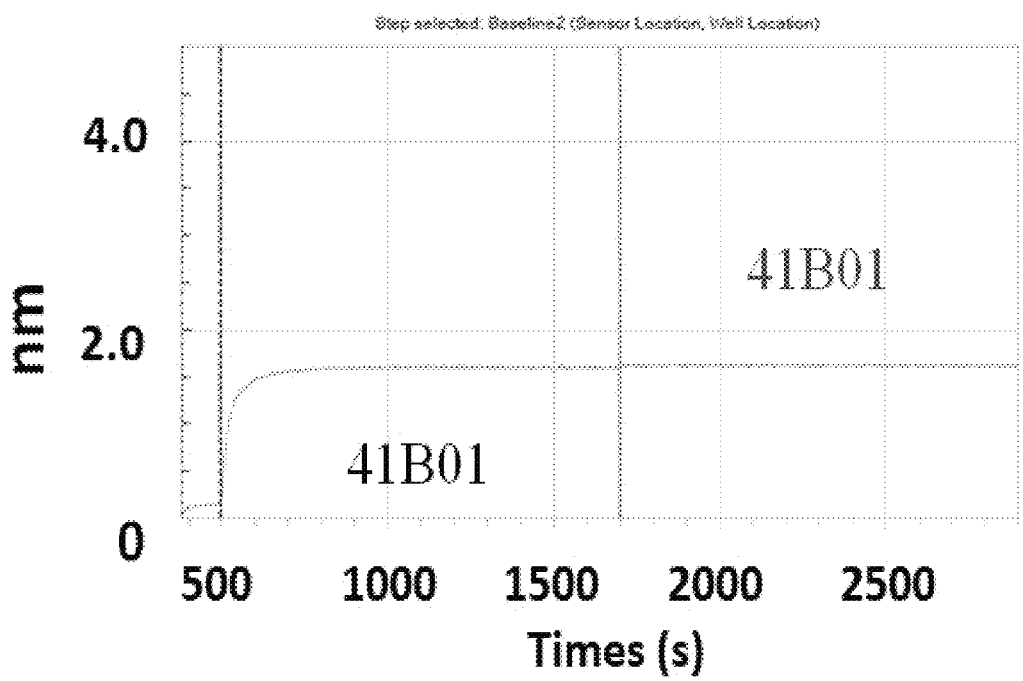
FIGS. 11A-11D show cross-competition between 41B01 and 41B02.
Figure 11B:
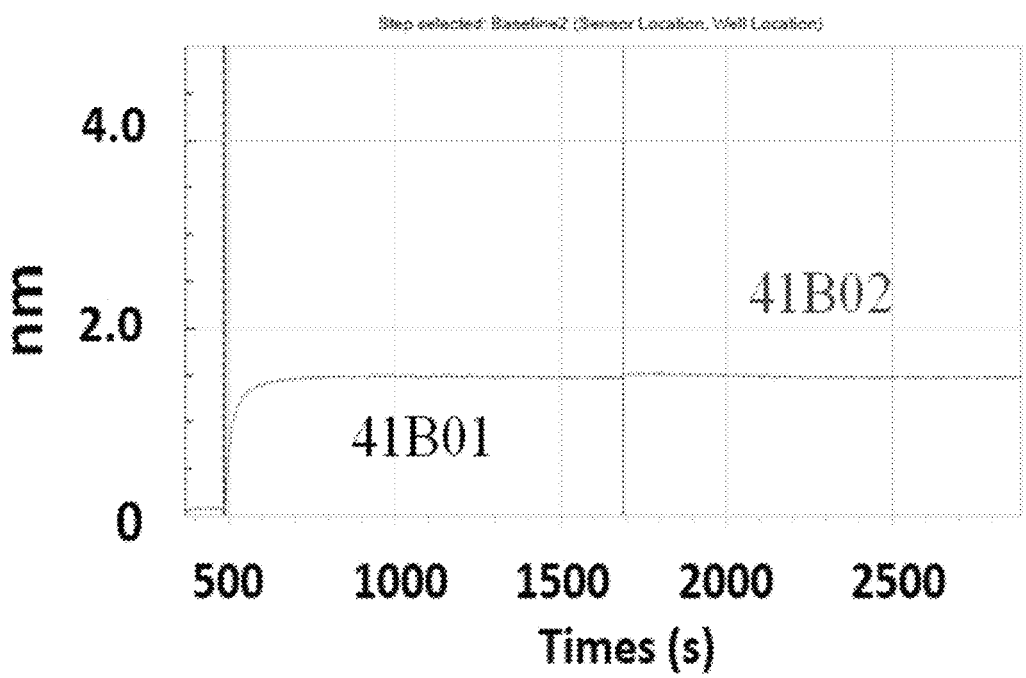
Figure 11C:
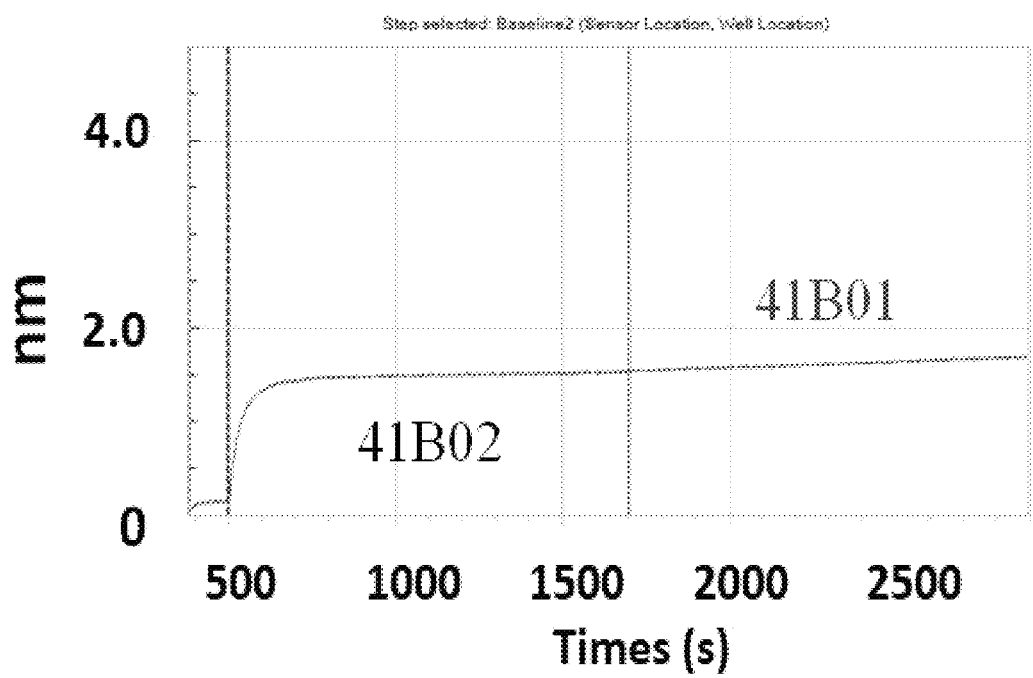
Figure 11D:
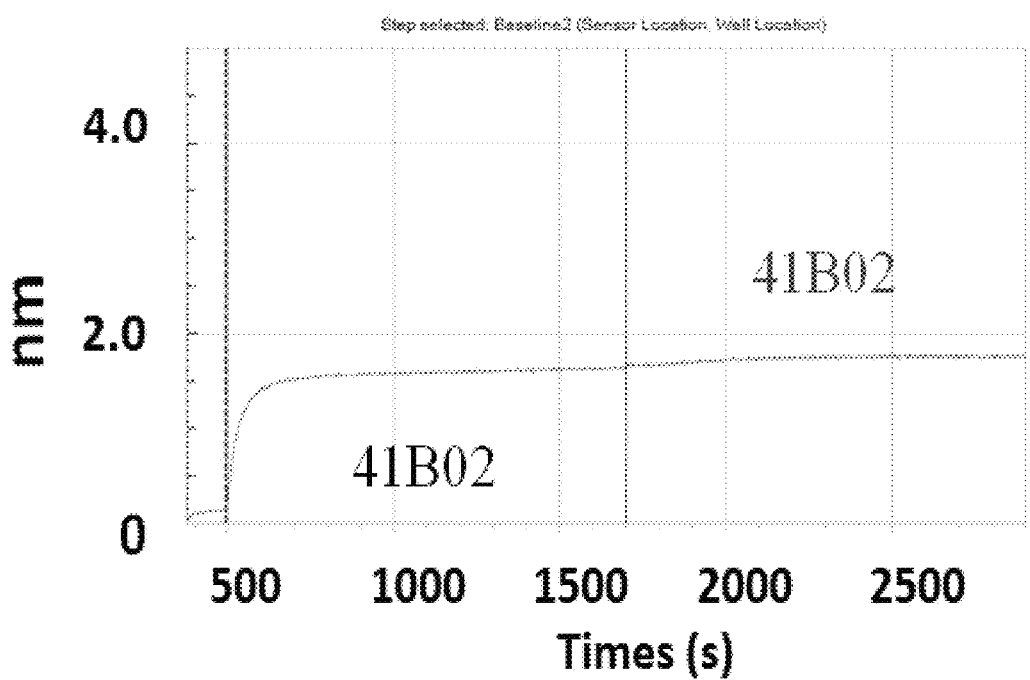

FIGS. 11A-11D show cross-competition between 41B01 and 41B02. Competition assay was performed between two candidates (41B01 and 41B02). Recombinant human 41BB-His tag protein was firstly fixed on the biosensor. Then primary and secondary antibodies were sequentially associated with the biosensor to detect binding competition between two antibodies. Overall, binding competition was observed between 41B01 and 41B02, indicating that these two candidates have same epitope against 41BB. FIG. 11A shows results of self-binding of 41B01, FIG. 11B shows results of 41B01 as a 1st antibody and 41B02 as a $2^{nd}$ antibody, FIG. 11C shows results of 41B02 as a $1^{st}$ antibody and 41B01 as a $2^{nd}$ antibody, and FIG. 11D shows results of self-binding of 41B02.

Figure 12A:
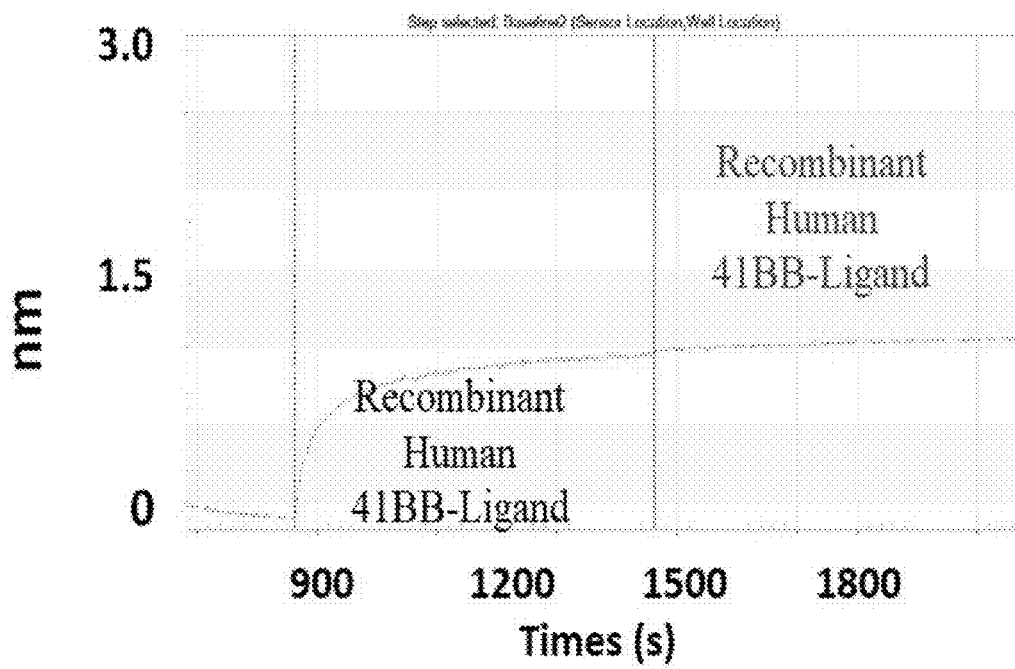
Figure 12B:
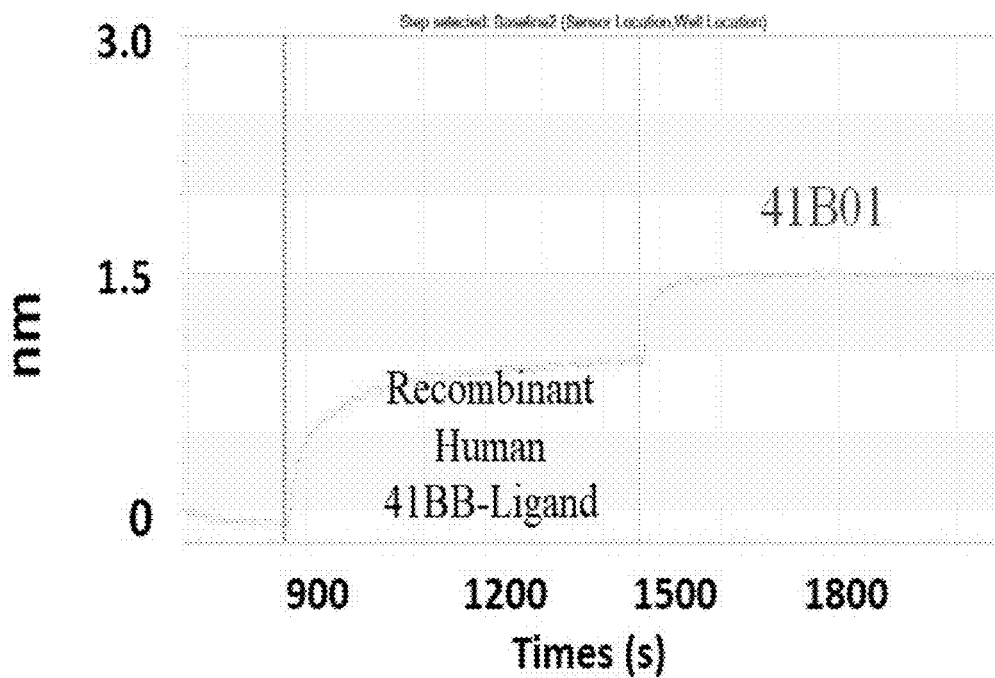

FIGS. 12A-12C show cross-competition between recombinant human 41BB-ligand and 41B01. Competition assay was performed between recombinant human 41BB-ligand and 41B01. Recombinant human 41BB-His tag protein was firstly fixed on the biosensor. Then recombinant human 41BB-ligand and 41B01 were sequentially associated with the biosensor to detect binding competition between them. Overall, binding competition was not observed between recombinant human 41BB-ligand and 41B01, indicating that 41B01 has unique binding site to 41BB compared to recombinant human 41BB-ligand. FIG. 12A shows results of self-binding of recombinant human 41BB-ligand, FIG. 12B shows results of recombinant human 41BB-ligand as a $1^{st}$ antibody and 41B01 as a $2^{nd}$ antibody, and FIG. 12C shows results of 41B01 as a 1st antibody and recombinant human 41BB-ligand as a $2^{nd}$ antibody.

Figure 3:
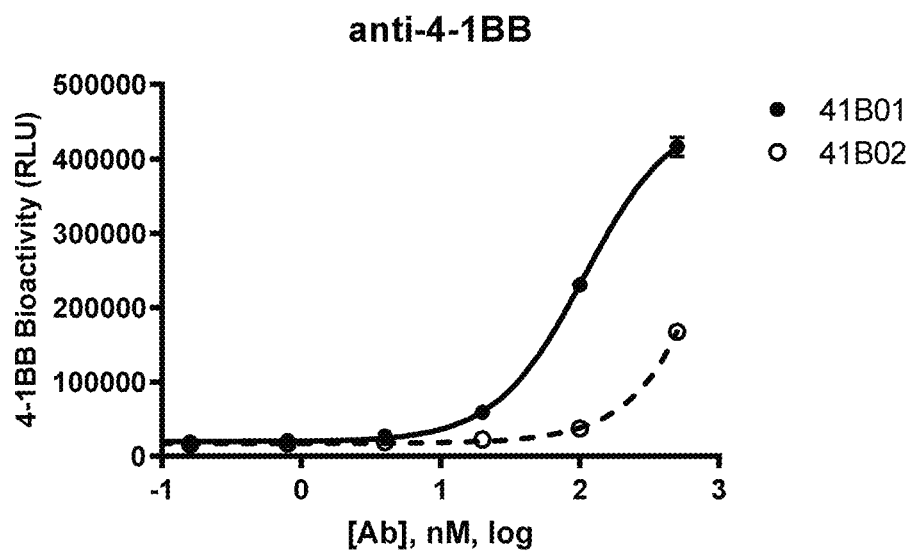
FIG. 3 is the graph that shows the 4-1BB signal activation by the anti-4-1BB antibody prepared according to one embodiment of the present invention.

Example 2. Activities of Anti-4-1BB Antibodies (1) Activity of the Anti-4-1BB Antibodies to Promote 4-1BB Signal To test the ability of anti-4-1BB antibodies to promote 4-1BB signal, cell-based 4-1BB assay was used. In this assay, GloResponse™ NFκB-luc2/4-1BB Jurkat cell line (Promega, cat #CS196004) was used. GloResponse™ NFκB-luc2/4-1BB Jurkat cell line is genetically modified to stably express 4-11313 receptors and luciferase downstream of a response element. Luciferase expression is induced upon antibody binding to the 4-1BB receptors. In brief, 25 μL of antibodies crosslinked with anti-human IgG Fc secondary antibodies (starting from 500 nM diluted for 5-fold) were added to the plate. Harvest GloResponse™ NFκB-luc2/4-1BB Jurkat cell line and dispense 50 μL of GloResponse™ NFκB-luc2/4-1BB Jurkat cell line per well to make 5×104 cells per well to plate. Culture 6 hrs in 37° C.+5% CO2 humidified incubator. During incubation time reconstitute Bio-Glo™ reagent according to the manufacturer's instruction. After 6 hrs incubation, add 75 per well of Bio-Glo™ Reagent to the assay plate. Wait 5 minutes and measure luminescence using microplate reader. Four-parameter logistic curve analysis was performed with GraphPad software. The obtained results are shown in FIG. 3. As shown in FIG. 3, the anti-4-1BB antibodies tested showed 4-1BB agonistic activity.

Figure 4:
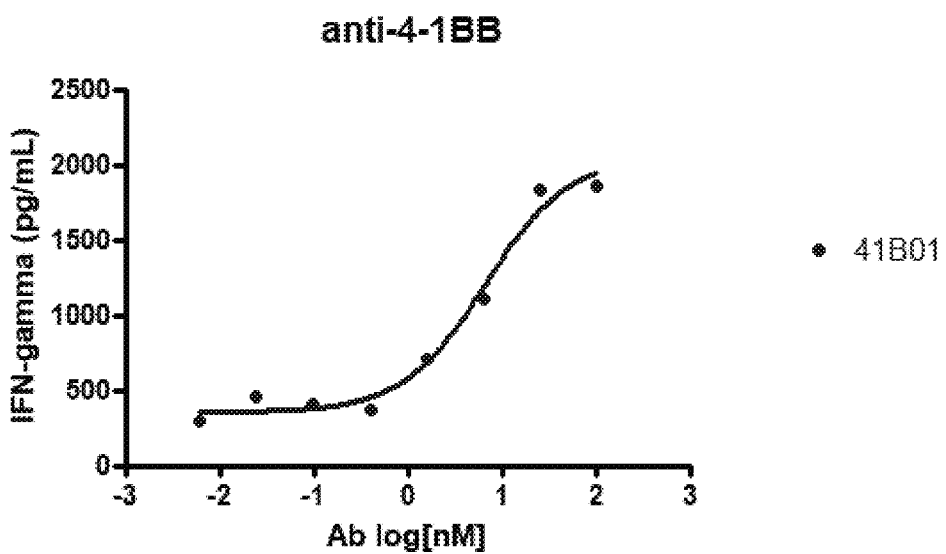
FIG. 4 is the graph that shows the T-cell activation by the anti-4-1BB antibody prepared according to one embodiment of the present invention.

(2) Activity of the Anti-4-1BB Antibodies to Promote Human T Cell Immune Response To test the ability of anti-4-1BB antibodies to stimulated human PBMCs response, cytokine production assay was used. Human PBMCs stimulated with human anti-CD3 antibody were used as the effector cells. HCC-1954 cells which no expressed 4-1BB was used as the target cells. In this system, PBMCs ($3\times10^4$) were co-cultured with HCC-1954 ($1\times10^4$) in the presence of human anti-CD3 antibody. Anti-4-1BB antibodies (starting from 100 nM (=15 ug/mL) diluted for 10 dose) and Fc crosslinked antibodies (starting from 500 nM (=75 ug/mL) diluted for 10 dose) were added to the mixed culture. The obtained results are shown in FIG. 4. As shown in FIG. 4, anti-4-1BB antibodies induced cytokine release.

(3) Activities of PD-L1×4-1BB Antibodies to Promote 4-1BB Signal

The 4-1BB signal promotion by the 4-1BB antibody in the form of bispecific antibodies was measured using cell-based 4-1BB assay.

The bispecific antibody, PD-L1×4-1BB bispecific antibody, consisted of heavy components and light components as follows:

(1) Heavy Components (N'→C')
  1) heavy chain of anti-PD-L1 antibody: SEQ ID NO: 63,
  2) linker: SEQ ID NO: 66 (GGGGSGGGGSGGGGS), and
  3) anti-4-1BB scFv, 41B01 (scFv) (Table 10) or 41B02 (scFv) (Table 14), prepared in Example 1.2; and (2) Light Components (N'→C')
  Light chain of anti-PD-L1 antibody: SEQ ID NO: 64.

In this assay, GloResponse™ NFκB-luc2/4-1BB Jurkat cell line (Promega, cat #CS196004) was used as effector cells and PD-L1-expressing or not expressing cancer cell line as target cells. GloResponse™ NFκB-luc2/4-1BB Jurkat cell line is genetically modified to stably express 4-1BB and luciferase downstream of a response element. Luciferase expression is induced upon antibody binding to the 4-1BB receptor. In brief, plate HCC1954 (expressing PD-L1) at $2.5\times10^4$ cells per well in a white 96-well assay plate in 100 μL culture medium (RPMI1640+10% FBS). Culture overnight in 37° C.+5% xCO2 humidified incubator. After overnight culture, remove 100 μL of culture medium and dispense 25 μL of Assay Medium (RPMI1640+1% FBS) to pre-plated target cells. 25 μL of each bispecific antibody (starting from 15 nM diluted for 8-fold or 1.5 nM diluted for 4-fold) were added to the plate. Harvest GloResponse™ NFκB-luc2/4-1BB Jurkat cell line and resuspend with Assay Medium. Dispense 25 μL of GloResponse™ NFκB-luc2/4-1BB Jurkat cell line per well to make $2.5\times10^4$ cells per well to plate. Culture 6 hrs in 37° C.+5% CO2 humidified incubator. During incubation time reconstitute Bio-Glo™ reagent according to the manufacturer's instruction. After 6 hrs incubation, add 75 per well of Bio-Glo™ Reagent to the assay plate. Wait 5 minutes and measure luminescence using microplate reader. Four-parameter logistic curve analysis was performed with GraphPad software.

Figure 5:
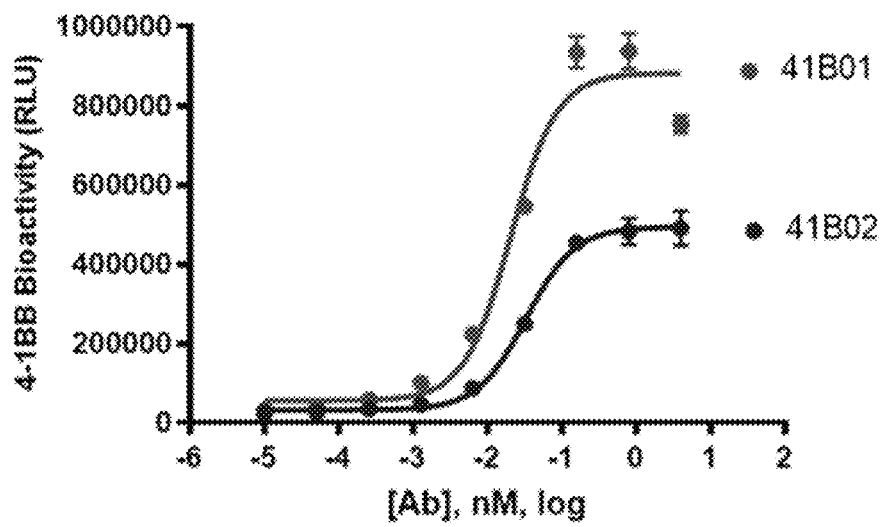
FIG. 5 is the graph that shows the 4-1BB signal activation by the anti-4-1BB antibody prepared according to one embodiment of the present invention, in the form of bispecific antibody.

The obtained results are shown in FIG. 5, wherein 41B01 indicates a PD-L1×4-1BB bispecific antibody comprising 41B01 (scFv) and 41B02 indicates a PD-L1×4-1BB bispecific antibody comprising 41B02 (scFv). As shown in FIG. 5, when the 4-1BB antibodies were constructed in the form of bispecific antibody (PD-L1×4-1BB bispecific antibody), the PD-L1×4-1BB bispecific antibodies tested showed stronger 4-1BB signal activation in the presence of tumor antigen (PD-L1), compared to anti PD-L1 monoclonal antibodies applied alone.

(4) In Vivo Efficacy of Anti-4-1BB Antibodies

Humanized mice that express the extracellular domain of human 4-1BB were used. Mouse colon adenocarcinoma cells (MC38) were engineered to express human PD-L1. Humanized mice (h4-1BB) were subcutaneously implanted with MC38-hPD-L1 cells. Mouse were intraperitoneally administered Q3D for 5 times (five time injection of the antibody every three days) with following antibodies: human IgG type control (10 mg/kg), and anti-4-1BB antibody (41B01, 10 mg/kg).

Figure 6:
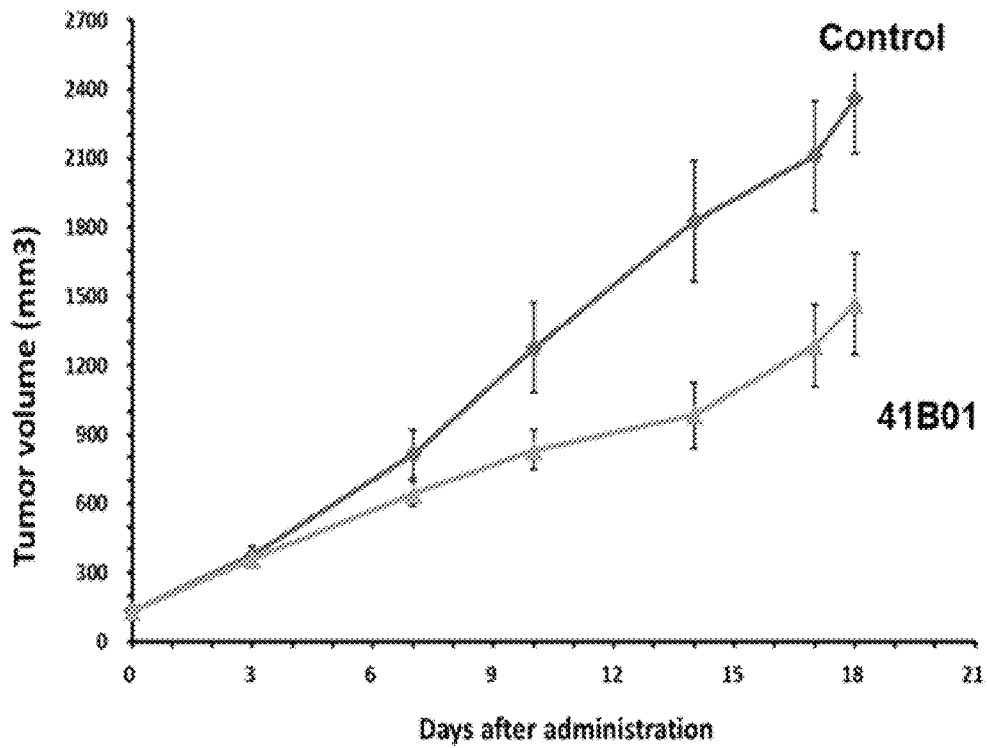
FIG. 6 is the graph that shows a cancer-inhibiting efficacy in a mouse tumor syngeneic model, of the anti-4-1BB antibody prepared according to one embodiment of the present invention. It was shown that each anti-4-1BB antibody inhibited the growth of cancer in human 4-1BB knock-in mouse. This result means that the 4-1BB antibody of the present invention binds to immune cell expressing human 4-1BB, thereby inhibiting the growth of cancer, and being usefully used as a cancer therapeutic agent.

Tumor volumes were monitored by caliper measurement twice per week for the duration of the experiment, and the obtained results are shown in FIG. 6. Tumor growth inhibition induced by the anti-4-1BB antibody using 41B01 was significantly greater than that observed with the combination of each targeting monoclonal antibodies (See FIG. 6).

As shown in FIG. 6, the anti-4-1BB antibody has increased in vivo anti-tumor effect compared to hIgG (control).

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

The invention claimed is:

1. An isolated anti-tumor necrosis factor receptor superfamily member 9 (anti-4-1BB) antibody or an antigen-binding fragment thereof, wherein (a) the anti-4-1BB antibody or (b) the anti-4-1BB antibody antigen-binding fragment comprises:
   (a) a heavy chain complementarity determining region 1 (CDR-H1) of SEQ ID NO: 1, a heavy chain complementarity determining region 2 (CDR-H2) of SEQ ID NO: 4, a heavy chain complementarity determining region 3 (CDR-H3) of SEQ ID NO: 7, a light chain complementarity determining region 1 (CDR-L1) of SEQ ID NO: 12, a light chain complementarity determining region 2 (CDR-L2) of SEQ ID NO: 14, and A light chain complementarity determining region 3 (CDR-L3) of SEQ ID NO: 16;
   (b) a CDR-H1 of SEQ ID NO: 1, a CDR-H2 of SEQ ID NO: 4, a CDR-H3 of SEQ ID NO: 8, a VL CDR1 of SEQ ID NO: 12, a VL CDR2 of SEQ ID NO: 14, and a VL CDR3 of SEQ ID NO: 16;
   (c) a CDR-H1 of SEQ ID NO: 1, a CDR-H2 of SEQ ID NO: 4, a CDR-H3 of SEQ ID NO: 9, a VL CDR1 of SEQ ID NO: 12, a VL CDR2 of SEQ ID NO: 14, and a VL CDR3 of SEQ ID NO: 16;
(d) a CDR-H1 of SEQ ID NO: 2, a CDR-H2 of SEQ ID NO: 5, a CDR-H3 of SEQ ID NO: 10, a VL CDR1 of SEQ ID NO: 12, a VL CDR2 of SEQ ID NO: 14, and a VL CDR3 of SEQ ID NO: 16; or
(e) a CDR-H1 of SEQ ID NO: 3, a CDR-H2 of SEQ ID NO: 6, a CDR-H3 of SEQ ID NO: 11, a VL CDR1 of SEQ ID NO: 13, a VL CDR2 of SEQ ID NO: 15, and a VL CDR3 of SEQ ID NO: 17.

2. The anti-4-1BB antibody or an antigen-binding fragment thereof according to claim 1, wherein (a) the anti-4-1BB antibody or (b) the anti-4-1BB antibody antigen-binding fragment comprises:
(1) a heavy chain variable region of SEQ ID NO: 18, and a light chain variable region of SEQ ID NO: 24;
(2) a heavy chain variable region of SEQ ID NO: 19, and a light chain variable region of SEQ ID NO: 24;
(3) a heavy chain variable region of SEQ ID NO: 20, and a light chain variable region of SEQ ID NO: 24;
(4) a heavy chain variable region of SEQ ID NO: 19, and a light chain variable region of SEQ ID NO: 25;
(5) a heavy chain variable region of SEQ ID NO: 20, and a light chain variable region of SEQ ID NO: 25;
(6) a heavy chain variable region of SEQ ID NO: 21, and a light chain variable region of SEQ ID NO: 24;
(7) a heavy chain variable region of SEQ ID NO: 22, and a light chain variable region of SEQ ID NO: 25;
(8) a heavy chain variable region of SEQ ID NO: 23, and a light chain variable region of SEQ ID NO: 26;
(9) a heavy chain variable region of SEQ ID NO: 57, and a light chain variable region of SEQ ID NO: 61;
(10) a heavy chain variable region of SEQ ID NO: 58, and a light chain variable region of SEQ ID NO: 61;
(11) a heavy chain variable region of SEQ ID NO: 58, and a light chain variable region of SEQ ID NO: 62;
(12) a heavy chain variable region of SEQ ID NO: 39, and a light chain variable region of SEQ ID NO: 62;
(13) a heavy chain variable region of SEQ ID NO: 59, and a light chain variable region of SEQ ID NO: 61; or
(14) a heavy chain variable region of SEQ ID NO: 60, and a light chain variable region of SEQ ID NO: 62.

3. The anti-4-1BB antibody or an antigen-binding fragment thereof according to claim 1, wherein (a) the anti-4-1BB antibody or (b) the anti-4-1BB antibody antigen-binding fragment comprises:
(i) a heavy chain of SEQ ID NO: 27 and a light chain of SEQ ID NO: 33;
(ii) a heavy chain of SEQ ID NO: 28 and a light chain of SEQ ID NO: 33;
(iii) a heavy chain of SEQ ID NO: 29 and a light chain of SEQ ID NO: 33;
(iv) a heavy chain of SEQ ID NO: 28 and a light chain of SEQ ID NO: 34;
(v) a heavy chain of SEQ ID NO: 29 and a light chain of SEQ ID NO: 34;
(vi) a heavy chain of SEQ ID NO: 30 and a light chain of SEQ ID NO: 33;
(vii) a heavy chain of SEQ ID NO: 31 and a light chain of SEQ ID NO: 34; or
(viii) a heavy chain of SEQ ID NO: 32 and a light chain of SEQ ID NO: 35.

4. The anti-4-1BB antibody or an antigen-binding fragment thereof according to claim 1, wherein anti-4-1BB antibody antigen-binding fragment is an anti-4-1BB single-chain variable fragment (scFv) comprising:
a light chain variable region of SEQ ID NO: 61 and a heavy chain variable region of SEQ ID NO: 57;
a light chain variable region of SEQ ID NO: 61 and a heavy chain variable region of SEQ ID NO: 58;
a light chain variable region of SEQ ID NO: 62 and a heavy chain variable region of SEQ ID NO: 58;
a light chain variable region of SEQ ID NO: 62 and a heavy chain variable region of SEQ ID NO: 39;
a light chain variable region of SEQ ID NO: 61 and a heavy chain variable region of SEQ ID NO: 59; or
a light chain variable region of SEQ ID NO: 62 and a heavy chain variable region of SEQ ID NO: 60.

* * * * *

```
                         SEQUENCE LISTING

<160> NUMBER OF SEQ ID NOS: 69

<210> SEQ ID NO 1
<211> LENGTH: 5
<212> TYPE: PRT
<213> ORGANISM: Artificial Sequence
<220> FEATURE:
<223> OTHER INFORMATION: Synthetic_CDR-H1 of anti-4-1BB antibody

<400> SEQUENCE: 1
```

```
Ser Tyr Asp Met Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic_CDR-H1 of anti-4-1BB antibody

<400> SEQUENCE: 2

Gly Tyr Asp Met Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic_CDR-H1 of anti-4-1BB antibody

<400> SEQUENCE: 3

Ser Asn Val Met Asn
1               5

<210> SEQ ID NO 4
<211> LENGTH: 17
<212> TYPE: PRT
<213> ORGANISM: Artificial Sequence
<220> FEATURE:
<223> OTHER INFORMATION: Synthetic_CDR-H2 of anti-4-1BB antibody

<400> SEQUENCE: 4

Trp Ile Ser Tyr Ser Gly Gly Ser Ile Tyr Tyr Ala Asp Ser Val Lys
1               5                   10                  15

Gly

<210> SEQ ID NO 5
<211> LENGTH: 17
<212> TYPE: PRT
<213> ORGANISM: Artificial Sequence
<220> FEATURE:
<223> OTHER INFORMATION: Synthetic_CDR-H2 of anti-4-1BB antibody

<400> SEQUENCE: 5

Val Ile Tyr Pro Asp Asp Gly Asn Thr Tyr Tyr Ala Asp Ser Val Lys
1               5                   10                  15

Gly

<210> SEQ ID NO 6
<211> LENGTH: 16
<212> TYPE: PRT
<213> ORGANISM: Artificial Sequence
<220> FEATURE:
<223> OTHER INFORMATION: Synthetic_CDR-H2 of anti-4-1BB antibody

<400> SEQUENCE: 6

Glu Ile Ser His Ser Gly Ser Thr Asn Tyr Asn Pro Ser Leu Lys Ser
1               5                   10                  15

<210> SEQ ID NO 7
<211> LENGTH: 12
<212> TYPE: PRT
<213> ORGANISM: Artificial Sequence
<220> FEATURE:
<223> OTHER INFORMATION: Synthetic_CDR-H3 of anti-4-1BB antibody
```

```
<400> SEQUENCE: 7

Asp Gly Gln Arg Asn Ser Met Arg Glu Phe Asp Tyr
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic_CDR-H3 of anti-4-1BB antibody

<400> SEQUENCE: 8

Asp Ala Gln Arg Asn Ser Met Arg Glu Phe Asp Tyr
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic_CDR-H3 of anti-4-1BB antibody

<400> SEQUENCE: 9

Asp Ala Gln Arg Gln Ser Met Arg Glu Phe Asp Tyr
1               5                   10

<210> SEQ ID NO 10
<211> LENGTH: 18
<212> TYPE: PRT
<213> ORGANISM: Artificial Sequence
<220> FEATURE:
<223> OTHER INFORMATION: Synthetic_CDR-H3 of anti-4-1BB antibody

<400> SEQUENCE: 10

His Gly Gly Gln Lys Pro Thr Thr Lys Ser Ser Ser Ala Tyr Gly Met
1               5                   10                  15

Asp Gly

<210> SEQ ID NO 11
<211> LENGTH: 7
<212> TYPE: PRT
<213> ORGANISM: Artificial Sequence
<220> FEATURE:
<223> OTHER INFORMATION: Synthetic_CDR-H3 of anti-4-1BB antibody

<400> SEQUENCE: 11

Gly Ala Gly Asn Leu Gly Tyr
1               5

<210> SEQ ID NO 12
<211> LENGTH: 13
<212> TYPE: PRT
<213> ORGANISM: Artificial Sequence
<220> FEATURE:
<223> OTHER INFORMATION: Synthetic_CDR-L1 of anti-4-1BB antibody

<400> SEQUENCE: 12

Ser Gly Ser Ser Ser Asn Ile Gly Asn Asn Tyr Val Thr
1               5                   10

<210> SEQ ID NO 13
<211> LENGTH: 11
<212> TYPE: PRT
<213> ORGANISM: Artificial Sequence
<220> FEATURE:
```

```
<223> OTHER INFORMATION: Synthetic_CDR-L1 of anti-4-1BB antibody

<400> SEQUENCE: 13

Gln Ala Ser Gln Asp Ile Ser Asn Tyr Leu Asn
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Synthetic_CDR-L2 of anti-4-1BB antibody

<400> SEQUENCE: 14

Ala Asp Ser His Arg Pro Ser
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic_CDR-L2 of anti-4-1BB antibody

<400> SEQUENCE: 15

Gly Ala Ser Ser Arg Ala Thr
1               5

<210> SEQ ID NO 16
<211> LENGTH: 11
<212> TYPE: PRT
<213> ORGANISM: Artificial Sequence
<220> FEATURE:
<223> OTHER INFORMATION: Synthetic_CDR-L3 of anti-4-1BB antibody

<400> SEQUENCE: 16

Ala Thr Trp Asp Tyr Ser Leu Ser Gly Tyr Val
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Synthetic_CDR-L3 of anti-4-1BB antibody

<400> SEQUENCE: 17

Gln Gln Tyr Asn Ser Tyr Pro Ile Thr
1               5

<210> SEQ ID NO 18
<211> LENGTH: 121
<212> TYPE: PRT
<213> ORGANISM: Artificial Sequence
<220> FEATURE:
<223> OTHER INFORMATION: Synthetic_Heavy chain variable region of anti-
      4-1BB antibody

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Asp Met Ser Trp Val Arg Gln Ala Pro Gly Lys Gly Leu Glu Trp Val
            35                  40                  45
```

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gln Arg Asn Ser Met Arg Glu Phe Asp Tyr Trp Gly
            100                 105                 110

Gln Gly Thr Leu Val Thr Val Ser Ser
        115                 120

<210> SEQ ID NO 19
<211> LENGTH: 121
<212> TYPE: PRT
<213> ORGANISM: Artificial Sequence
<220> FEATURE:
<223> OTHER INFORMATION: Synthetic_Heavy chain variable region of anti-
      4-1BB antibody

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Asn Ser Met Arg Glu Phe Asp Tyr Trp Gly
            100                 105                 110

Gln Gly Thr Leu Val Thr Val Ser Ser
        115                 120

<210> SEQ ID NO 20
<211> LENGTH: 121
<212> TYPE: PRT
<213> ORGANISM: Artificial Sequence
<220> FEATURE:
<223> OTHER INFORMATION: Synthetic_Heavy chain variable region of anti-
      4-1BB antibody

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Gln Ser Met Arg Glu Phe Asp Tyr Trp Gly
            100                 105                 110

Gln Gly Thr Leu Val Thr Val Ser Ser
        115                 120

<210> SEQ ID NO 21
<211> LENGTH: 127
<212> TYPE: PRT
<213> ORGANISM: Artificial Sequence
<220> FEATURE:
<223> OTHER INFORMATION: Synthetic_Heavy chain variable region of anti-
      4-1BB antibody

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Gly Leu Glu Trp Val
        35                  40                  45

Ser Val Ile Tyr Pro Asp Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys His Gly Gly Gln Lys Pro Thr Thr Lys Ser Ser Ser Ala Tyr
            100                 105                 110

Gly Met Asp Gly Trp Gly Gln Gly Thr Leu Val Thr Val Ser Ser
        115                 120                 125

<210> SEQ ID NO 22
<211> LENGTH: 127
<212> TYPE: PRT
<213> ORGANISM: Artificial Sequence
<220> FEATURE:
<223> OTHER INFORMATION: Synthetic_Heavy chain variable region of anti-
      4-1BB antibody

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Gly Leu Glu Trp Val
        35                  40                  45

Ser Val Ile Tyr Pro Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Gly Gly Gln Lys Pro Thr Thr Lys Ser Ser Ser Ala Tyr
            100                 105                 110

Gly Met Asp Gly Trp Gly Gln Gly Thr Leu Val Thr Val Ser Ser
        115                 120                 125

<210> SEQ ID NO 23
<211> LENGTH: 115

```
<212> TYPE: PRT
<213> ORGANISM: Artificial Sequence
<220> FEATURE:
<223> OTHER INFORMATION: Synthetic_Heavy chain variable region of anti-
      4-1BB antibody

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Val Met Asn Trp Val Arg Gln Ala Pro Gly Lys Gly Leu Glu Trp Val
        35                  40                  45

Ser Glu Ile Ser His Ser Gly Ser Thr Asn Tyr Asn Pro Ser Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Val Gly Ala Gly Asn Leu Gly Tyr Trp Gly Gln Gly Thr Leu Val Thr
            100                 105                 110

Val Ser Ser
        115

<210> SEQ ID NO 24
<211> LENGTH: 110
<212> TYPE: PRT
<213> ORGANISM: Artificial Sequence
<220> FEATURE:
<223> OTHER INFORMATION: Synthetic_Light chain variable region of anti-
      4-1BB antibody

<400> SEQUENCE: 24

Gln Ser Val Leu Thr Gln Pro Pro Ser Ala Ser Gly Thr Pro Gly Arg
1               5                   10                  15

Arg Val Thr Ile Ser Cys Ser Gly Ser Ser Ser Asn Ile Gly Asn Asn
            20                  25                  30

Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu
            100                 105                 110

<210> SEQ ID NO 25
<211> LENGTH: 110
<212> TYPE: PRT
<213> ORGANISM: Artificial Sequence
<220> FEATURE:
<223> OTHER INFORMATION: Synthetic_Light chain variable region of anti-
      4-1BB antibody

<400> SEQUENCE: 25

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
```

```
                    20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu
            100                 105                 110

<210> SEQ ID NO 26
<211> LENGTH: 108
<212> TYPE: PRT
<213> ORGANISM: Artificial Sequence
<220> FEATURE:
<223> OTHER INFORMATION: Synthetic_Light chain variable region of anti-
      4-1BB antibody

<400> SEQUENCE: 26

Glu Ile Val Leu Thr Gln Ser Pro Gly Thr Leu Ser Leu Ser Pro Gly
1               5                   10                  15

Glu Arg Ala Thr Leu Ser Cys Gln Ala Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asn Ser Tyr Pro Ile
                85                  90                  95

Thr Phe Gly Gln Gly Thr Lys Leu Glu Ile Lys Arg
            100                 105

<210> SEQ ID NO 27
<211> LENGTH: 448
<212> TYPE: PRT
<213> ORGANISM: Artificial Sequence
<220> FEATURE:
<223> OTHER INFORMATION: Synthetic_Heavy chain of anti-4-1BB antibody

<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gln Arg Asn Ser Met Arg Glu Phe Asp Tyr Trp Gly
            100                 105                 110
```

```
Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
        210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
        260                 265                 270

Glu Val Gln Phe Asn Trp Tyr Val Asp Gly Val Glu Val His Asn Ala
    275                 280                 285

Lys Thr Lys Pro Arg Glu Glu Gln Phe Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
        420                 425                 430

Leu His Asn His Tyr Thr Gln Lys Ser Leu Ser Leu Ser Leu Gly Lys
        435                 440                 445

<210> SEQ ID NO 28
<211> LENGTH: 448
<212> TYPE: PRT
<213> ORGANISM: Artificial Sequence
<220> FEATURE:
<223> OTHER INFORMATION: Synthetic_Heavy chain of anti-4-1BB antibody

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Asp Met Ser Trp Val Arg Gln Ala Pro Gly Lys Gly Leu Glu Trp Val
        35                  40                  45

Ser Trp Ile Ser Tyr Ser Gly Gly Ser Ile Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ala Gln Arg Asn Ser Met Arg Glu Phe Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
        420                 425                 430

Leu His Asn His Tyr Thr Gln Lys Ser Leu Ser Leu Ser Leu Gly Lys
    435                 440                 445
```

-continued

```
<210> SEQ ID NO 29
<211> LENGTH: 448
<212> TYPE: PRT
<213> ORGANISM: Artificial Sequence
<220> FEATURE:
<223> OTHER INFORMATION: Synthetic_Heavy chain of anti-4-1BB antibody

<400> SEQUENCE: 29
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Gln Ser Met Arg Glu Phe Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

```
Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
                435                 440                 445

<210> SEQ ID NO 30
<211> LENGTH: 454
<212> TYPE: PRT
<213> ORGANISM: Artificial Sequence
<220> FEATURE:
<223> OTHER INFORMATION: Synthetic_Heavy chain of anti-4-1BB antibody

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Gly Leu Glu Trp Val
        35                  40                  45

Ser Val Ile Tyr Pro Asp Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys His Gly Gly Gln Lys Pro Thr Thr Lys Ser Ser Ser Ala Tyr
            100                 105                 110

Gly Met Asp Gly Trp Gly Gln Gly Thr Leu Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
        195                 200                 205

Thr Cys Asn Val Asp His Lys Pro Ser Asn Thr Lys Val Asp Lys Arg
    210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
        275                 280                 285
```

Val Glu Val His Asn Ala Lys Thr Lys Pro Arg Glu Glu Gln Phe Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Gln Glu Glu Met Thr Lys Asn
                355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
                420                 425                 430

Ser Val Met His Glu Ala Leu His Asn His Tyr Thr Gln Lys Ser Leu
                435                 440                 445

Ser Leu Ser Leu Gly Lys
    450

<210> SEQ ID NO 31
<211> LENGTH: 454
<212> TYPE: PRT
<213> ORGANISM: Artificial Sequence
<220> FEATURE:
<223> OTHER INFORMATION: Synthetic_Heavy chain of anti-4-1BB antibody

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Gly Leu Glu Trp Val
        35                  40                  45

Ser Val Ile Tyr Pro Asp Asp Gly Asn Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Gly Gly Gln Lys Pro Thr Thr Lys Ser Ser Ser Ala Tyr
                100                 105                 110

Gly Met Asp Gly Trp Gly Gln Gly Thr Leu Val Thr Val Ser Ser Ala
            115                 120                 125

Ser Thr Lys Gly Pro Ser Val Phe Pro Leu Ala Pro Cys Ser Arg Ser
130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

```
Ser Ser Val Val Thr Val Pro Ser Ser Leu Gly Thr Lys Thr Tyr
            195                 200                 205

Thr Cys Asn Val Asp His Lys Pro Ser Asn Thr Lys Val Asp Lys Arg
    210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Gln Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Leu Gly Lys
    450

<210> SEQ ID NO 32
<211> LENGTH: 442
<212> TYPE: PRT
<213> ORGANISM: Artificial Sequence
<220> FEATURE:
<223> OTHER INFORMATION: Synthetic_Heavy chain of anti-4-1BB antibody

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Val Met Asn Trp Val Arg Gln Ala Pro Gly Lys Gly Leu Glu Trp Val
        35                  40                  45

Ser Glu Ile Ser His Ser Gly Ser Thr Asn Tyr Asn Pro Ser Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95
```

```
Val Gly Ala Gly Asn Leu Gly Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Cys Ser Arg Ser Thr Ser Glu Ser Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
            195                 200                 205

Val Asp Lys Arg Val Glu Ser Lys Tyr Gly Pro Pro Cys Pro Pro Cys
210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
            245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
            275                 280                 285

Glu Gln Phe Asn Ser Thr Tyr Arg Val Val Ser Val Leu Thr Val Leu
290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
            325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
            405                 410                 415

Val Phe Ser Cys Ser Val Met His Glu Ala Leu His Asn His Tyr Thr
            420                 425                 430

Gln Lys Ser Leu Ser Leu Ser Leu Gly Lys
            435                 440

<210> SEQ ID NO 33
<211> LENGTH: 216
<212> TYPE: PRT
<213> ORGANISM: Artificial Sequence
<220> FEATURE:
<223> OTHER INFORMATION: Synthetic_Light chain of anti-4-1BB antibody

<400> SEQUENCE: 33

Gln Ser Val Leu Thr Gln Pro Pro Ser Ala Ser Gly Thr Pro Gly Arg
1               5                   10                  15
```

```
Arg Val Thr Ile Ser Cys Ser Gly Ser Ser Asn Ile Gly Asn Asn
             20                  25                  30

Tyr Val Thr Trp Tyr Gln Gln Leu Pro Gly Thr Ala Pro Lys Leu Leu
             35                  40                  45

Ile Tyr Ala Asp Ser His Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Thr Trp Asp Tyr Ser Leu
                 85                  90                  95

Ser Gly Tyr Val Phe Gly Gly Gly Thr Lys Leu Thr Val Leu Gly Gln
                100                 105                 110

Pro Lys Ala Ala Pro Ser Val Thr Leu Phe Pro Pro Ser Ser Glu Glu
                115                 120                 125

Leu Gln Ala Asn Lys Ala Thr Leu Val Cys Leu Ile Ser Asp Phe Tyr
            130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
                195                 200                 205

Thr Val Ala Pro Ala Glu Cys Ser
                210                 215

<210> SEQ ID NO 34
<211> LENGTH: 216
<212> TYPE: PRT
<213> ORGANISM: Artificial Sequence
<220> FEATURE:
<223> OTHER INFORMATION: Synthetic_Light chain of anti-4-1BB antibody

<400> SEQUENCE: 34

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
             20                  25                  30

Tyr Val Thr Trp Tyr Gln Gln Leu Pro Gly Thr Ala Pro Lys Leu Leu
             35                  40                  45

Ile Tyr Ala Asp Ser His Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Thr Trp Asp Tyr Ser Leu
                 85                  90                  95

Ser Gly Tyr Val Phe Gly Gly Gly Thr Lys Leu Thr Val Leu Gly Gln
                100                 105                 110

Pro Lys Ala Ala Pro Ser Val Thr Leu Phe Pro Pro Ser Ser Glu Glu
                115                 120                 125

Leu Gln Ala Asn Lys Ala Thr Leu Val Cys Leu Ile Ser Asp Phe Tyr
            130                 135                 140

Pro Gly Ala Val Thr Val Ala Trp Lys Ala Asp Ser Ser Pro Val Lys
145                 150                 155                 160
```

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys Ser
    210                 215

<210> SEQ ID NO 35
<211> LENGTH: 108
<212> TYPE: PRT
<213> ORGANISM: Artificial Sequence
<220> FEATURE:
<223> OTHER INFORMATION: Synthetic_Light chain of anti-4-1BB antibody

<400> SEQUENCE: 35

Glu Ile Val Leu Thr Gln Ser Pro Gly Thr Leu Ser Leu Ser Pro Gly
1               5                   10                  15

Glu Arg Ala Thr Leu Ser Cys Gln Ala Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asn Ser Tyr Pro Ile
                85                  90                  95

Thr Phe Gly Gln Gly Thr Lys Leu Glu Ile Lys Arg
            100                 105

<210> SEQ ID NO 36
<211> LENGTH: 327
<212> TYPE: PRT
<213> ORGANISM: Artificial Sequence
<220> FEATURE:
<223> OTHER INFORMATION: Synthetic_Heavy chain constant region

<400> SEQUENCE: 36

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 37
<211> LENGTH: 106
<212> TYPE: PRT
<213> ORGANISM: Artificial Sequence
<220> FEATURE:
<223> OTHER INFORMATION: Synthetic_Light chain constant region

<400> SEQUENCE: 37

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
        50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ser
            100                 105

<210> SEQ ID NO 38
<211> LENGTH: 106
<212> TYPE: PRT
<213> ORGANISM: Artificial Sequence
<220> FEATURE:
<223> OTHER INFORMATION: Synthetic_Light chain constant region

<400> SEQUENCE: 38

Thr Val Ala Ala Pro Ser Val Phe Ile Phe Pro Pro Ser Asp Glu Gln

```
1               5                   10                  15
Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
            50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 39
<211> LENGTH: 121
<212> TYPE: PRT
<213> ORGANISM: Artificial Sequence
<220> FEATURE:
<223> OTHER INFORMATION: Synthetic_Heavy chain variable region of anti-
      4-1BB scFv

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Cys Leu Glu Trp Val
            35                  40                  45

Ser Trp Ile Ser Tyr Ser Gly Gly Ser Ile Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Gln Ser Met Arg Glu Phe Asp Tyr Trp Gly
            100                 105                 110

Gln Gly Thr Leu Val Thr Val Ser Ser
        115                 120

<210> SEQ ID NO 40
<211> LENGTH: 30
<212> TYPE: PRT
<213> ORGANISM: Artificial Sequence
<220> FEATURE:
<223> OTHER INFORMATION: Synthetic_H-FR1 of anti-4-1BB antibody

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 41
<211> LENGTH: 14
<212> TYPE: PRT
<213> ORGANISM: Artificial Sequence
<220> FEATURE:
<223> OTHER INFORMATION: Synthetic_H-FR2 of anti-4-1BB antibody
```

```
<400> SEQUENCE: 41

Trp Val Arg Gln Ala Pro Gly Lys Gly Leu Glu Trp Val Ser
1               5                   10

<210> SEQ ID NO 42
<211> LENGTH: 32
<212> TYPE: PRT
<213> ORGANISM: Artificial Sequence
<220> FEATURE:
<223> OTHER INFORMATION: Synthetic_H-FR3 of anti-4-1BB antibody

<400> SEQUENCE: 42

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
                20                  25                  30

<210> SEQ ID NO 43
<211> LENGTH: 32
<212> TYPE: PRT
<213> ORGANISM: Artificial Sequence
<220> FEATURE:
<223> OTHER INFORMATION: Synthetic_H-FR3 of anti-4-1BB antibody

<400> SEQUENCE: 43

Arg Phe Thr Ile Ser Arg Asp Asn Ser Lys Asn Thr Leu Tyr Leu Gln
1               5                   10                  15

Met Asn Ser Leu Arg Ala Glu Asp Ala Ala Val Tyr Tyr Cys Ala Lys
                20                  25                  30

<210> SEQ ID NO 44
<211> LENGTH: 32
<212> TYPE: PRT
<213> ORGANISM: Artificial Sequence
<220> FEATURE:
<223> OTHER INFORMATION: Synthetic_H-FR3 of anti-4-1BB antibody

<400> SEQUENCE: 44

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
                20                  25                  30

<210> SEQ ID NO 45
<211> LENGTH: 32
<212> TYPE: PRT
<213> ORGANISM: Artificial Sequence
<220> FEATURE:
<223> OTHER INFORMATION: Synthetic_H-FR3 of anti-4-1BB antibody

<400> SEQUENCE: 45

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Val
                20                  25                  30

<210> SEQ ID NO 46
<211> LENGTH: 11
<212> TYPE: PRT
<213> ORGANISM: Artificial Sequence
<220> FEATURE:
<223> OTHER INFORMATION: Synthetic_H-FR4 of anti-4-1BB antibody

<400> SEQUENCE: 46
```

Trp Gly Gln Gly Thr Leu Val Thr Val Ser Ser
1               5                   10

<210> SEQ ID NO 47
<211> LENGTH: 22
<212> TYPE: PRT
<213> ORGANISM: Artificial Sequence
<220> FEATURE:
<223> OTHER INFORMATION: Synthetic_L-FR1 of anti-4-1BB antibody

<400> SEQUENCE: 47

Gln Ser Val Leu Thr Gln Pro Pro Ser Ala Ser Gly Thr Pro Gly Arg
1               5                   10                  15

Arg Val Thr Ile Ser Cys
            20

<210> SEQ ID NO 48
<211> LENGTH: 22
<212> TYPE: PRT
<213> ORGANISM: Artificial Sequence
<220> FEATURE:
<223> OTHER INFORMATION: Synthetic_L-FR1 of anti-4-1BB antibody

<400> SEQUENCE: 48

Gln Ser Val Leu Thr Gln Pro Pro Ser Ala Ser Gly Thr Pro Gly Gln
1               5                   10                  15

Arg Val Thr Ile Ser Cys
            20

<210> SEQ ID NO 49
<211> LENGTH: 23
<212> TYPE: PRT
<213> ORGANISM: Artificial Sequence
<220> FEATURE:
<223> OTHER INFORMATION: Synthetic_L-FR1 of anti-4-1BB antibody

<400> SEQUENCE: 49

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 50
<211> LENGTH: 15
<212> TYPE: PRT
<213> ORGANISM: Artificial Sequence
<220> FEATURE:
<223> OTHER INFORMATION: Synthetic_L-FR2 of anti-4-1BB antibody

<400> SEQUENCE: 50

Trp Tyr Gln Gln Leu Pro Gly Thr Ala Pro Lys Leu Leu Ile Tyr
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Synthetic_L-FR2 of anti-4-1BB antibody

<400> SEQUENCE: 51

Trp Tyr Gln Gln Lys Pro Gly Gln Ala Pro Arg Leu Leu Ile Tyr
1               5                   10                  15

<210> SEQ ID NO 52

```
<211> LENGTH: 32
<212> TYPE: PRT
<213> ORGANISM: Artificial Sequence
<220> FEATURE:
<223> OTHER INFORMATION: Synthetic_L-FR3 of anti-4-1BB antibody

<400> SEQUENCE: 52

Gly Val Pro Asp Arg Phe Ser Gly Ser Lys Ser Gly Thr Ser Ala Ser
1               5                   10                  15

Leu Ala Ile Ser Gly Leu Arg Ser Glu Asp Glu Ala Asp Tyr Tyr Cys
            20                  25                  30

<210> SEQ ID NO 53
<211> LENGTH: 32
<212> TYPE: PRT
<213> ORGANISM: Artificial Sequence
<220> FEATURE:
<223> OTHER INFORMATION: Synthetic_L-FR3 of anti-4-1BB antibody

<400> SEQUENCE: 53

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 54
<211> LENGTH: 10
<212> TYPE: PRT
<213> ORGANISM: Artificial Sequence
<220> FEATURE:
<223> OTHER INFORMATION: Synthetic_L-FR4 of anti-4-1BB antibody

<400> SEQUENCE: 54

Phe Gly Gly Gly Thr Lys Leu Thr Val Leu
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Synthetic_L-FR4 of anti-4-1BB antibody

<400> SEQUENCE: 55

Phe Gly Gln Gly Thr Lys Leu Glu Ile Lys Arg
1               5                   10

<210> SEQ ID NO 56
<211> LENGTH: 20
<212> TYPE: PRT
<213> ORGANISM: Artificial Sequence
<220> FEATURE:
<223> OTHER INFORMATION: Synthetic_Peptide linker

<400> SEQUENCE: 56

Gly Gly Gly Gly Ser Gly Gly Gly Gly Ser Gly Gly Gly Gly Ser Gly
1               5                   10                  15

Gly Gly Ser
            20

<210> SEQ ID NO 57
<211> LENGTH: 121
<212> TYPE: PRT
<213> ORGANISM: Artificial Sequence
<220> FEATURE:
<223> OTHER INFORMATION: Synthetic_Heavy chain variable region of anti-
```

```
                          4-1BB scFv

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Cys Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gln Arg Asn Ser Met Arg Glu Phe Asp Tyr Trp Gly
            100                 105                 110

Gln Gly Thr Leu Val Thr Val Ser Ser
        115                 120

<210> SEQ ID NO 58
<211> LENGTH: 121
<212> TYPE: PRT
<213> ORGANISM: Artificial Sequence
<220> FEATURE:
<223> OTHER INFORMATION: Synthetic_Heavy chain variable region of anti-
      4-1BB scFv

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Cys Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Asn Ser Met Arg Glu Phe Asp Tyr Trp Gly
            100                 105                 110

Gln Gly Thr Leu Val Thr Val Ser Ser
        115                 120

<210> SEQ ID NO 59
<211> LENGTH: 127
<212> TYPE: PRT
<213> ORGANISM: Artificial Sequence
<220> FEATURE:
<223> OTHER INFORMATION: Synthetic_Heavy chain variable region of anti-
      4-1BB scFv

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30
```

```
Asp Met Ser Trp Val Arg Gln Ala Pro Gly Lys Cys Leu Glu Trp Val
        35                  40                  45

Ser Val Ile Tyr Pro Asp Asp Gly Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Ala Ala Val Tyr Tyr Cys
                85                  90                  95

Ala Lys His Gly Gly Gln Lys Pro Thr Thr Lys Ser Ser Ser Ala Tyr
            100                 105                 110

Gly Met Asp Gly Trp Gly Gln Gly Thr Leu Val Thr Val Ser Ser
        115                 120                 125

<210> SEQ ID NO 60
<211> LENGTH: 127
<212> TYPE: PRT
<213> ORGANISM: Artificial Sequence
<220> FEATURE:
<223> OTHER INFORMATION: Synthetic_Heavy chain variable region of anti-
      4-1BB scFv

<400> SEQUENCE: 60

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Gly Tyr
                20                  25                  30

Asp Met Ser Trp Val Arg Gln Ala Pro Gly Lys Cys Leu Glu Trp Val
        35                  40                  45

Ser Val Ile Tyr Pro Asp Asp Gly Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys His Gly Gly Gln Lys Pro Thr Thr Lys Ser Ser Ser Ala Tyr
            100                 105                 110

Gly Met Asp Gly Trp Gly Gln Gly Thr Leu Val Thr Val Ser Ser
        115                 120                 125

<210> SEQ ID NO 61
<211> LENGTH: 110
<212> TYPE: PRT
<213> ORGANISM: Artificial Sequence
<220> FEATURE:
<223> OTHER INFORMATION: Synthetic_Light chain variable region of anti-
      4-1BB scFv

<400> SEQUENCE: 61

Gln Ser Val Leu Thr Gln Pro Pro Ser Ala Ser Gly Thr Pro Gly Arg
 1               5                  10                  15

Arg Val Thr Ile Ser Cys Ser Gly Ser Ser Ser Asn Ile Gly Asn Asn
                20                  25                  30

Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80
```

```
Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu
            100                 105                 110

<210> SEQ ID NO 62
<211> LENGTH: 110
<212> TYPE: PRT
<213> ORGANISM: Artificial Sequence
<220> FEATURE:
<223> OTHER INFORMATION: Synthetic_Light chain variable region of anti-
      4-1BB scFv

<400> SEQUENCE: 62

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu
            100                 105                 110

<210> SEQ ID NO 63
<211> LENGTH: 449
<212> TYPE: PRT
<213> ORGANISM: Artificial Sequence
<220> FEATURE:
<223> OTHER INFORMATION: Synthetic_Heavy Chain of anti-PD-L1 antibody

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
            35                  40                  45

Ala Thr Ile Ser Asp Ala Gly Gly Tyr Ile Tyr Tyr Arg Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Leu Pro Trp Arg Tyr Ala Leu Asp Tyr Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160
```

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
        435                 440                 445

Lys

<210> SEQ ID NO 64
<211> LENGTH: 214
<212> TYPE: PRT
<213> ORGANISM: Artificial Sequence
<220> FEATURE:
<223> OTHER INFORMATION: Synthetic_Light Chain of anti-PD-L1 antibody

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro

Glu Asp Ile Ala Thr Tyr Tyr Cys Gln Gln His Tyr Thr Thr Pro Leu
            65                  70                  75                  80

Thr Phe Gly Gln Gly Thr Lys Leu Glu Ile Lys Arg Thr Val Ala Ala
                    85                  90                  95

Pro Ser Val Phe Ile Phe Pro Ser Asp Glu Gln Leu Lys Ser Gly
            100                 105                 110

Thr Ala Ser Val Val Cys Leu Leu Asn Asn Phe Tyr Pro Arg Glu Ala
                    115                 120                 125

Lys Val Gln Trp Lys Val Asp Asn Ala Leu Gln Ser Gly Asn Ser Gln
130                 135                 140

Glu Ser Val Thr Glu Gln Asp Ser Lys Asp Ser Thr Tyr Ser Leu Ser
145                 150                 155                 160

Ser Thr Leu Thr Leu Ser Lys Ala Asp Tyr Glu Lys His Lys Val Tyr
                    165                 170                 175

Ala Cys Glu Val Thr His Gln Gly Leu Ser Ser Pro Val Thr Lys Ser
            180                 185                 190

Phe Asn Arg Gly Glu Cys
    195                 200

205

<210> SEQ ID NO 65
<211> LENGTH: 449
<212> TYPE: PRT
<213> ORGANISM: Artificial Sequence
<220> FEATURE:
<223> OTHER INFORMATION: Synthetic_Heavy Chain of anti-PD-L1 antibody

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys

```
                210                 215                 220
Thr His Thr Cys Pro Pro Cys Pro Ala Pro Glu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Ala Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 66
<211> LENGTH: 15
<212> TYPE: PRT
<213> ORGANISM: Artificial Sequence
<220> FEATURE:
<223> OTHER INFORMATION: Synthetic_Peptide linker

<400> SEQUENCE: 66

Gly Gly Gly Gly Ser Gly Gly Gly Ser Gly Gly Gly Gly Ser
1               5                   10                  15

<210> SEQ ID NO 67
<211> LENGTH: 255
<212> TYPE: PRT
<213> ORGANISM: Artificial Sequence
<220> FEATURE:
<223> OTHER INFORMATION: Synthetic_4-1BB protein (NP_001552.2)

<400> SEQUENCE: 67

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
```

```
                50                  55                  60
Cys Arg Gln Cys Lys Gly Val Phe Arg Thr Arg Lys Glu Cys Ser Ser
 65                  70                  75                  80

Thr Ser Asn Ala Glu Cys Asp Cys Thr Pro Gly Phe His Cys Leu Gly
                 85                  90                  95

Ala Gly Cys Ser Met Cys Glu Gln Asp Cys Lys Gln Gly Gln Glu Leu
                100                 105                 110

Thr Lys Lys Gly Cys Lys Asp Cys Cys Phe Gly Thr Phe Asn Asp Gln
                115                 120                 125

Lys Arg Gly Ile Cys Arg Pro Trp Thr Asn Cys Ser Leu Asp Gly Lys
                130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
                180                 185                 190

Ala Leu Thr Ser Thr Ala Leu Leu Phe Leu Leu Phe Phe Leu Thr Leu
                195                 200                 205

Arg Phe Ser Val Val Lys Arg Gly Arg Lys Lys Leu Leu Tyr Ile Phe
                210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 68
<211> LENGTH: 10
<212> TYPE: PRT
<213> ORGANISM: Artificial Sequence
<220> FEATURE:
<223> OTHER INFORMATION: Synthetic_Peptide linker

<400> SEQUENCE: 68

Gly Gly Gly Gly Ser Gly Gly Gly Gly Ser
1               5                   10

<210> SEQ ID NO 69
<211> LENGTH: 18
<212> TYPE: PRT
<213> ORGANISM: Artificial Sequence
<220> FEATURE:
<223> OTHER INFORMATION: Synthetic_Peptide linker

<400> SEQUENCE: 69

Gly Ser Gly Ser Gly Ser Gly Ser Gly Ser Gly Ser Gly Ser Gly Ser
1               5                   10                  15
Gly Ser
```